United States Patent
Mande et al.

(10) Patent No.: US 11,062,808 B2
(45) Date of Patent: Jul. 13, 2021

(54) METHOD AND SYSTEM FOR EARLY RISK ASSESSMENT OF PRETERM DELIVERY OUTCOME

(71) Applicant: Tata Consultancy Services Limited, Mumbai (IN)

(72) Inventors: Sharmila Shekhar Mande, Pune (IN); Mohammed Monzoorul Haque, Pune (IN); Anirban Dutta, Pune (IN); Nishal Kumar Pinna, Pune (IN); Mitali Merchant, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 0 days.

(21) Appl. No.: 16/076,622

(22) PCT Filed: Feb. 15, 2017

(86) PCT No.: PCT/IB2017/050840
§ 371 (c)(1),
(2) Date: Aug. 8, 2018

(87) PCT Pub. No.: WO2017/141169
PCT Pub. Date: Aug. 24, 2017

(65) Prior Publication Data
US 2019/0046105 A1    Feb. 14, 2019

(30) Foreign Application Priority Data
Feb. 16, 2016 (IN) .............................. 201621005426

(51) Int. Cl.
| | |
|---|---|
| *G16H 50/30* | (2018.01) |
| *A61B 5/00* | (2006.01) |
| *G16B 40/00* | (2019.01) |
| *C12Q 1/689* | (2018.01) |
| *G16B 30/00* | (2019.01) |

(52) U.S. Cl.
CPC ........... *G16H 50/30* (2018.01); *A61B 5/4343* (2013.01); *G16B 40/00* (2019.02); *C12Q 1/689* (2013.01); *G16B 30/00* (2019.02)

(58) Field of Classification Search
None
See application file for complete search history.

(56) References Cited

U.S. PATENT DOCUMENTS

| | | |
|---|---|---|
| 2006/0172330 A1 | 8/2006 | Osborn et al. |
| 2009/0299212 A1 | 12/2009 | Principe et al. |
| 2011/0152840 A1 | 6/2011 | Lee et al. |
| 2012/0270747 A1 | 10/2012 | Elovitz |
| 2014/0186332 A1 | 7/2014 | Ezrin et al. |
| 2014/0287948 A1 | 9/2014 | Boniface et al. |
| 2015/0259728 A1* | 9/2015 | Cutliffe ................. C12Q 1/689 514/789 |

FOREIGN PATENT DOCUMENTS

| | | |
|---|---|---|
| WO | WO-2014/152985 | 9/2014 |
| WO | WO-2015/153841 | 10/2015 |

OTHER PUBLICATIONS

Hyman, R. W. et al. Diversity of the Vaginal Microbiome Correlates With Preterm Birth. Reproductive Sciences 21, 32-40 (2014).*
Magurran, A. E. "An index of diversity . . . " Chapter 4 of Measuring Biological Diversity. (Blackwell Science Ltd, 2004). pp. 101-130.*
Zhu, X., Wang, J., Reyes-Gibby, C. & Shete, S. Processing and Analyzing Human Microbiome Data. in Statistical Human Genetics 850, 649-677 (2017).*
Newnham, J. P. et al. Strategies to prevent preterm birth. Frontiers in Immunology 5, 1-12 (2014).*
International Search Report dated Jul. 13, 2017, in counterpart International Application No. PCT/IB2017/050840; 1 page.
Written Opinion dated Jul. 13, 2017, in counterpart International Application No. PCT/IB2017/050840; 6 pages.

* cited by examiner

*Primary Examiner* — Soren Harward
(74) *Attorney, Agent, or Firm* — Finnegan, Henderson, Farabow, Garrett & Dunner LLP

(57) ABSTRACT

System and method for assessing preterm delivery risk for pregnant subject is disclosed. Existing preterm delivery risk assessment methods provide results in late second or third trimester of pregnancy, so little time is available for medical advice. Presently disclosed method and system predict preterm delivery risk within 15 weeks of pregnancy. Microbiome characterization data obtained from microbiome sample from pregnant subject. 'Microbial taxonomic abundance profile' generated from microbiome characterization data, contains abundance values of microbes present in the microbiome sample. 'Taxonomic Composition Skew' value, and distribution characteristic value for 'microbial taxonomic abundance profile', quantifying biases in abundance values of microbes from the microbial taxonomic abundance profile, is computed. Risk of preterm delivery is determined based on the distribution characteristic value or 'taxonomic composition skew' value of the set DSR, wherein the set DSR comprises values quantifying biases in the abundance values of microbes from the microbiome sample.

19 Claims, 6 Drawing Sheets

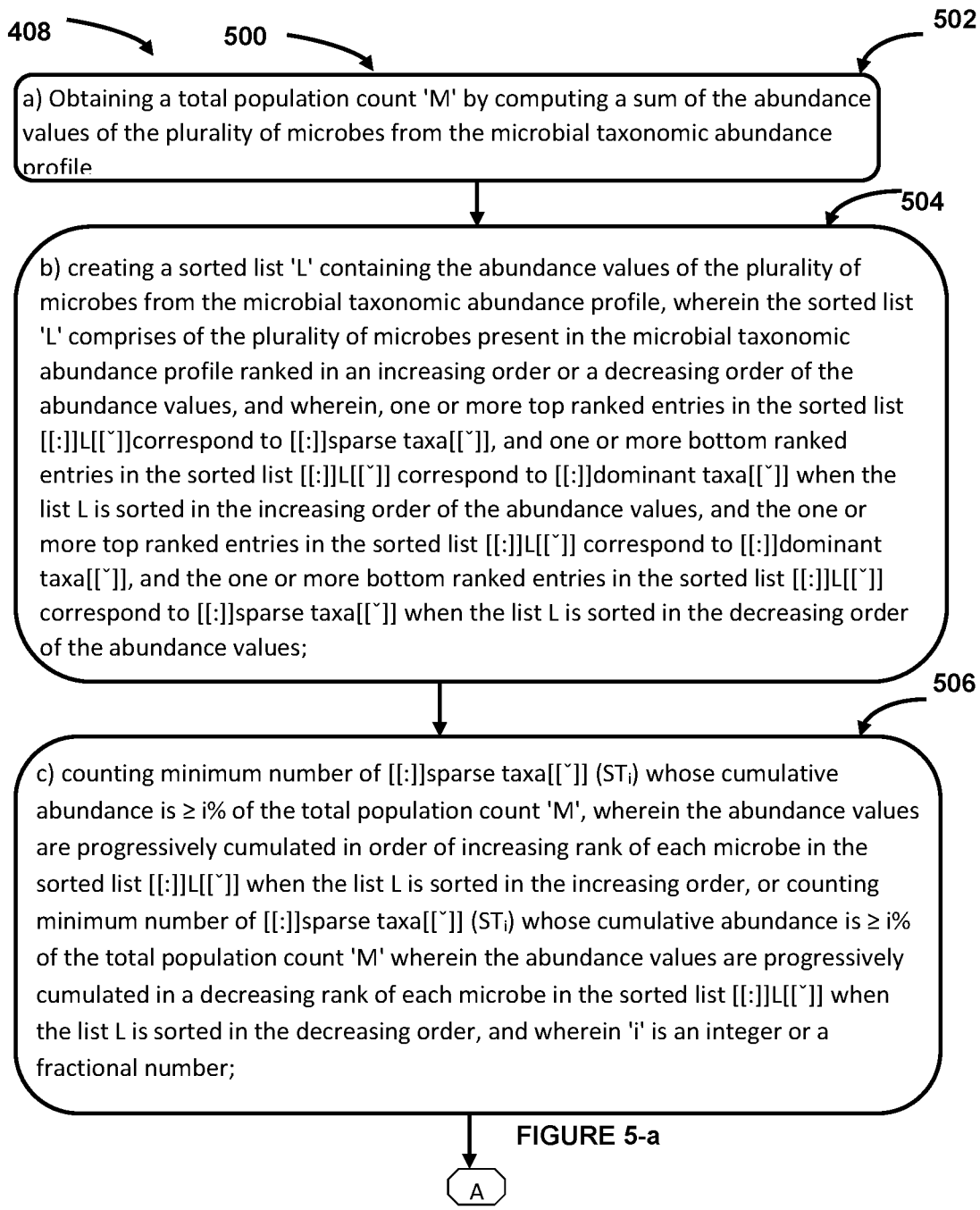
FIGURE 5-a

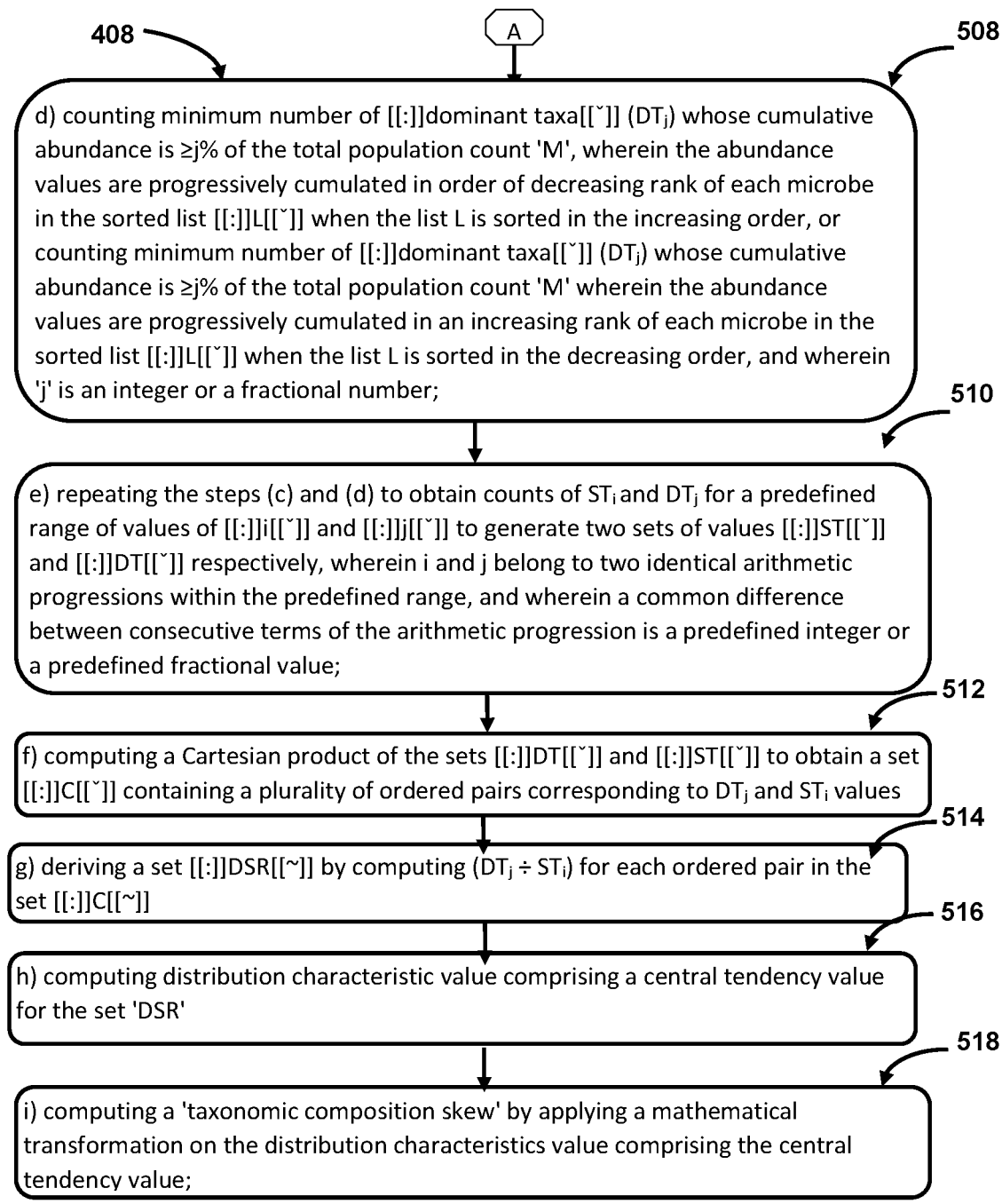
FIGURE 5-b

METHOD AND SYSTEM FOR EARLY RISK ASSESSMENT OF PRETERM DELIVERY OUTCOME

CROSS-REFERENCE TO RELATED APPLICATIONS AND PRIORITY

The present application claims priority to Indian Provisional Patent Application No. 201621005426, filed on Feb. 16, 2016, the entirety of which is hereby incorporated by reference.

TECHNICAL FIELD

The embodiments described herein generally relate to method and system for risk assessment of preterm delivery outcome of a pregnant subject, and more particularly to microbiome based method for early risk assessment of preterm delivery outcome of the pregnant subject.

BACKGROUND

Based on recent World Health Organization (WHO) estimates, preterm birth (i.e. birth before 37 completed weeks of pregnancy) is a leading cause of global neonate mortality. More children die due to preterm birth related complications as compared to that by diarrhea, malaria, or AIDS. Preterm delivery (PTD) cases are observed in 5%-18% of total pregnancies (www.who.int/mediacentre/factsheets/fs363/en/). Pre and/or post-partum costs associated with PTD outcomes are significantly high. PTD is typically associated with risks for both a mother as well as a delivered child. A significant proportion of preterm babies develop several life-threatening complications including moderate or severe respiratory distress, a compromised immune system, jaundice, anemia, cerebral palsy, and issues with vision and hearing. Given that, more than a million children die each year due to complications arising from preterm birth, research focused at diagnosis, prediction, and prevention of preterm births assumes high importance. There exists few physical and/or biochemical diagnostic markers for predicting risk of preterm birth, however these physical and/or biochemical diagnostic markers are mostly suitable for application in mid or late pregnancy stages.

Presently, the cascade of patho-physiologic events that cause preterm delivery (PTD) is not completely understood. However, a few intervention approaches e.g. progesterone supplementation, cervical cerclage, etc., that can potentially promote towards a healthy full-term gestation outcome, are available. Given this, diagnostic markers that can accurately indicate, at an early stage of pregnancy, the risk possibility of progression towards a preterm delivery outcome, holds a lot of significance. Currently, a number of diagnostic methods are available that can be employed at various stages of pregnancy to predict the risk of a preterm delivery outcome. However, amongst them, only a few are amenable for application in the early stages of pregnancy (i.e. the first trimester). Moreover, their overall accuracy (in terms of sensitivity and specificity) being low renders them unsuitable for usage in routine clinical practice. Furthermore, it may be noted that amongst existing PT B diagnostic methods, those having relatively better diagnostic/predictive ability, are mostly suited for application only in mid or late stages of pregnancy (i.e. second and third trimester of pregnancy). Although such diagnostic ability (in the mid or late stages of pregnancy) aids in a process of relocating the pregnant woman to a suitable medical setting (where the pregnant woman can be better/continuously monitored), the relatively short duration between the diagnosis and delivery makes it difficult for adopting meaningful intervention strategies that promote towards full-term healthy gestation. This highlights a current need for a diagnostic method that can predict, at a very early stage of pregnancy, ideally the first trimester, a possibility of a preterm delivery outcome. Such an early diagnostic/risk-assessment procedure will provide adequate time for medical practitioners to adopt available intervention/monitoring strategies that can potentially/possibly promote a full-term healthy gestation.

Further, many existing diagnostics techniques assessing the risk of a preterm delivery outcome rely on the pregnant subjects (a) presenting themselves with vaginal infections, (b) having abnormalities detected in radiological procedures, or (c) having a preterm history in earlier deliveries. Thus, relying on above discussed indicators makes such diagnostic techniques unsuitable in cases of first pregnancies or preterm outcomes which are not driven by known risk factors viz. vaginal infections and/or :fetal/uterine abnormalities. Moreover, some of the existing diagnostic methods require sampling techniques that are invasive in nature and thereby are likely to cause/inflict physical and/or emotional inconvenience to the subject undergoing the test.

Major drawback of the existing preterm delivery risk assessment methods is that these methods provide diagnostic results of practical utility only in the 'later' stages of pregnancy i.e. in the late second trimester or in the third (i.e. last) trimester of pregnancy. Therefore, very little time is available for subjects to take preventive or corrective medical advice to reduce or obviate the risk of preterm delivery. Hence, it is extremely important to accurately predict the risk of preterm delivery outcome in early stages of pregnancy, more particularly within 15 weeks of pregnancy (i.e. as early as possible in the pregnancy). Early prediction of preterm delivery outcome provides sufficient time for pregnant women/subject (detected with a risk of PTD) to take required precautionary or corrective medical procedures that can potentially reduce or obviate the risk of a preterm delivery outcome.

SUMMARY

The following description presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below. In view of the foregoing, an embodiment herein provides system and method for early risk assessment of preterm delivery outcome of a pregnant subject.

In one aspect of the present disclosure, a method for assessing a risk of preterm delivery for a pregnant subject is disclosed. In order to assess the risk of preterm delivery, a microbiome sample is obtained from the pregnant subject within first 15 weeks of pregnancy or within a first trimester of the pregnancy or within a second trimester of the pregnancy, and wherein the pregnant subject is a pregnant woman. The method comprises receiving, by a hardware processor, a microbial taxonomic abundance profile for the microbiome sample. The microbiome sample is obtained from the pregnant subject. The microbial taxonomic abundance profile contains abundance values of each of a plurality of microbes present in the microbiome sample. The method further comprises computing, by the hardware processor, at least one of a 'Taxonomic Composition Skew' value, and a distribution characteristic value for the microbial taxonomic abundance profile. The 'Taxonomic Composition Skew' value and the distribution characteristic value quantify biases in the abundance values of the plurality of microbes from the microbial taxonomic abundance profile. The computation of the Taxonomic Composition Skew value and the distribution characteristic value comprises, in step (a), obtaining a total population count 'M' by computing a sum of the abundance values of the plurality of microbes from the microbial taxonomic abundance profile. Further, in step (b), the method comprises creating a sorted list 'L' containing the abundance values of each of the plurality of microbes from the microbial taxonomic abundance profile. The sorted list 'L' comprises the abundance values of each of plurality of microbes present in the microbial taxonomic abundance profile ranked in an increasing order or a decreasing order of the abundance values. One or more top ranked entries in the sorted list L correspond to sparse taxa, and one or more bottom ranked entries in the sorted list L correspond to dominant taxa when the list L is sorted in the increasing order of the abundance values, and the one or more top ranked entries in the sorted list L correspond to dominant taxa, and the one or more bottom ranked entries in the sorted list L correspond to sparse taxa when the list L is sorted in the decreasing order of the abundance values. Further, in step (c), the method comprises counting minimum number of sparse taxa ($ST_i$) whose cumulative abundance is ≥i % of the total population count 'M', wherein the abundance values are progressively cumulated in order of an increasing rank of each microbe in the sorted list L when the list L is sorted in the increasing order, or counting minimum number of sparse taxa ($ST_i$) whose cumulative abundance is ≥i % of the total population count 'M', wherein the abundance values are progressively cumulated in order of decreasing rank of each microbe in the sorted list L when the list L is sorted in the decreasing order, and wherein 'i' is an integer or a fractional number. Further, in step (d), the method comprises, in one option, counting minimum number of dominant taxa ($DT_j$) whose cumulative abundance is ≥j % of the total population count 'M', wherein the abundance values are progressively cumulated in order of decreasing rank of each microbe in the sorted list L when the list L is sorted in the increasing order, or in another option the method comprises counting minimum number of dominant taxa ($DT_j$) whose cumulative abundance is ≥j % of the total population count 'M', wherein the abundance values are progressively cumulated in order of increasing rank of each microbe in the sorted list L when the list L is sorted in the decreasing order, and wherein 'j' is an integer or a fractional number. Further, in step (e), the steps c and d are repeated to obtain counts of $ST_i$ and $DT_j$ for a predefined range of values of i and j to generate two sets of values ST and DT respectively, wherein i and j belong to two identical arithmetic progressions within the predefined range, and wherein a common difference between consecutive terms of the arithmetic progression is a predefined integer or a predefined fractional value. Further, in step (f), the method comprises computing a Cartesian product of the sets DT and ST to obtain a set C containing a plurality of ordered pairs corresponding to $DT_j$ and $ST_i$ values, and in step (g), the method comprises deriving a set DSR by computing ($DT_j$, $ST_i$) for each ordered pair in the set C. After obtaining the set DSR, the method further, in step (h), comprises computing the distribution characteristic value of the set 'DSR', wherein the distribution characteristic value of the set 'DSR' comprises a central tendency value of the set DSR. Further, in step (i), the method comprises computing the 'taxonomic composition skew' value by applying a mathematical transformation on the distribution characteristic value comprising the central tendency value of the set DSR. The method further comprises determining, by the hardware processor, the risk of the preterm delivery for the pregnant subject based on at least one of the central tendency value of the set DSR, the distribution characteristic value of the set DSR, or the taxonomic composition skew value.

The method comprises obtaining, via microbiome characterization platform 108, microbiome characterization data of the microbiome sample, by applying one or more techniques comprising a sequencing technique, a microscopic examination, a flow cytometry method, an in-vitro culture based method, one or more enzymatic or fluorescence assays, or one or more assays involving spectroscopic identification and screening of signals from complex microbial populations, wherein the microbiome characterization data comprises sequenced microbial DNA data, a Microscopic imaging data, a Flow cytometry cellular measurement data, a colony count and cellular phenotypic data of microbes grown in in-vitro cultures, and a signal intensity data.

The method further comprises generating the microbial taxonomic abundance profile for the microbiome sample by computationally analyzing, by the hardware processor, the microbiome characterization data, using one or more taxonomic classification techniques.

In another aspect the method further comprises obtaining the sequenced microbial DNA data for the microbiome sample. Obtaining the sequenced microbial DNA data comprises isolating microbial DNA corresponding to the plurality of microbes present in the microbiome sample using at least one DNA extraction technique; and sequencing the microbial DNA using at least one DNA sequencing technique to obtain the sequenced microbial DNA data. The method further comprises generating the microbial taxonomic abundance profile for the microbiome sample by computationally analyzing, by the hardware processor, the sequenced microbial DNA data using one or more taxonomic classification techniques.

In another aspect of the present disclosure, a system 100 for assessing a risk of preterm delivery for a pregnant subject is disclosed. The system 100 comprises a computing system 102 further comprising a hardware processor 202; and a memory 206 coupled to the hardware processor 202. The hardware processor 202 executes a plurality of modules 208 stored in the memory 206. The plurality of modules 208 comprise a microbial taxonomic abundance profile generation module 210 and a computation module 212. The computation module 212 receives a microbial taxonomic abundance profile for a microbiome sample obtained from the pregnant subject. The microbial taxonomic abundance profile contains abundance values of a plurality of microbes present in the microbiome sample. The computation module 212 further computes, at least one of a 'Taxonomic Composition Skew' value, and a distribution characteristic value for the microbial taxonomic abundance profile. The 'Taxonomic Composition Skew' value and the distribution characteristic value quantify biases in the abundance values of the plurality of microbes from the microbial taxonomic abundance profile. In order to compute the Taxonomic Composition Skew value and the distribution characteristic value, the computation module 212, in step (a), obtains a total population count 'M' by computing a sum of the abundance values of the plurality of microbes from the microbial taxonomic abundance profile. Further, in step (b), the computation module 212, creates a sorted list 'L' containing the abundance values of the plurality of microbes from the microbial taxonomic abundance profile. The sorted list 'L' comprises of the abundance values of each of the plurality of microbes (i.e taxa) present in the microbial taxonomic abundance profile ranked in an increasing order or a decreasing order of the abundance values. One or more top ranked entries in the sorted list L correspond to sparse taxa, and one or more bottom ranked entries in the sorted list L correspond to dominant taxa, when the list L is sorted in the increasing order of the abundance values, and the one or more top ranked entries in the sorted list L correspond to dominant taxa, and the one or more bottom ranked entries in the sorted list L correspond to sparse taxa, when the list L is sorted in the decreasing order of the abundance values. Further, in step (c), the computation module 212, counts minimum number of sparse taxa ($ST_i$) whose cumulative abundance is $\geq i$ % of the total population count 'M', wherein the abundance values are progressively cumulated in order of increasing rank of each microbe in the sorted list L when the list L is sorted in the increasing order, or counting minimum number of sparse taxa ($ST_i$) whose cumulative abundance is $\geq i$ % of the total population count 'M' wherein the abundance values are progressively cumulated in a decreasing rank of each microbe in the sorted list L when the list L is sorted in the decreasing order, and wherein 'i' is an integer or a fractional number. Further, in step (d), the computation module 212, counts minimum number of dominant taxa ($DT_j$) whose cumulative abundance is $\geq j$ % of the total population count 'M', wherein the abundance values are progressively cumulated in order of decreasing rank of each microbe in the sorted list L when the list L is sorted in the increasing order, or counting minimum number of dominant taxa ($DT_j$) whose cumulative abundance is $\geq j$ % of the total population count 'M' wherein the abundance values are progressively cumulated in an increasing rank of each microbe in the sorted list L when the list L is sorted in the decreasing order, and wherein 'j' is an integer or a fractional number. Further, in step (e), the computation module 212, repeatedly executes the steps (c) and (d), to obtain counts of $ST_i$ and $DT_j$ for a predefined range of values of i and j to generate two sets of values ST and DT respectively, wherein i and j belong to two identical arithmetic progressions within the predefined range, and wherein a common difference between consecutive terms of the arithmetic progression is a predefined integer or a predefined fractional value. Further, in step (f), the computation module 212, computes a Cartesian product of the sets DT and ST to obtain a set C containing a plurality of ordered pairs corresponding to $DT_j$ and $ST_i$ values. Further, in step (g), the computation module 212, derives a set DSR by computing ($DT_j \div ST_i$) for each ordered pair in the set C. Further, in step (h), the computation module 212, computes the distribution characteristic value of the set 'DSR', wherein the distribution characteristic value of the set 'DSR' comprises a central tendency value of the set DSR. Further, in step (i), the computation module 212, computes the 'taxonomic composition skew' value by applying a mathematical transformation on the distribution characteristic value comprising the central tendency value of the set DSR. The computation module 212 determines the risk of the preterm delivery for the pregnant subject based on at least one of the central tendency value of the set DSR, the distribution characteristic value of the set DSR or the taxonomic composition skew value.

The system 100 comprises a microbiome sample receiver 110 and a microbiome characterization platform 108. The microbiome sample receiver 110 receives the microbiome sample from the pregnant subject. The microbiome characterization platform 108 comprises at least one of the sequencing platform 112, a microscopy platform 114, a nucleic acid hybridization platform 116, or a cell sorting platform 118 to obtain/generate the microbiome characterization data from the microbiome sample.

The microbiome characterization platform 108 receives the microbiome sample from the microbiome sample receiver 110. The microbiome characterization platform (108) obtains the microbiome characterization data from the microbiome sample by applying at least technique on the microbiome sample, wherein the at least one technique is selected from a group of techniques comprising a sequencing technique, a microscopic examination, a flow cytometry method, an in-vitro culture based method, one or more enzymatic or fluorescence assays, or one or more assays involving spectroscopic identification and screening of signals from complex microbial populations. The microbiome characterization data comprises sequenced microbial nucleic acid data, a Microscopic imaging data, a Flow cytometric cellular measurement data, a colony count and cellular phenotypic data of microbes grown in in-vitro cultures, and a signal intensity data.

In one aspect, the sequencing platform 112 receives the microbiome sample from the microbiome sample receiver 110. The sequencing platform 112 isolates microbial DNA corresponding to the plurality of microbes present in the microbiome sample using at least one DNA extraction technique. The sequencing platform 112 further sequences the microbial DNA using at least one DNA sequencing technique to obtain sequenced microbial DNA data. The microbial taxonomic abundance profile generation module 210 computationally analyzes the sequenced microbial DNA data using one or more taxonomic classification techniques to generate the microbial taxonomic abundance profile for the microbiome sample.

In another aspect of the present disclosure, a non-transitory computer readable medium embodying a program executable in a computing device by a hardware processor for assessing a risk of preterm delivery for a pregnant subject is disclosed. The program comprises a program code for receiving a microbial taxonomic abundance profile for a microbiome sample obtained from the pregnant subject, wherein the microbial taxonomic abundance profile contains abundance values of each of a plurality of microbes present in the microbiome sample. The program further comprises a program code for computing, at least one of a 'Taxonomic Composition Skew' value, and a distribution characteristic value for the microbial taxonomic abundance profile, wherein the 'Taxonomic Composition Skew' value and the distribution characteristic value quantify biases in the abundance values of the plurality of microbes from the microbial taxonomic abundance profile. The computation of the Taxonomic Composition Skew value and the distribution characteristic value comprises following steps (a) to (i). In step (a), obtaining a total population count 'M' by computing a sum of the abundance values of the plurality of microbes from the microbial taxonomic abundance profile. Further, in step (b), creating a sorted list 'L' containing the abundance values of each of the plurality of microbes from the microbial taxonomic abundance profile, wherein the sorted list 'L' comprises the abundance values of each of plurality of microbes present in the microbial taxonomic abundance profile ranked in an increasing order or a decreasing order of the abundance values, and wherein, one or more top ranked entries in the sorted list L correspond to sparse taxa, and one or more bottom ranked entries in the sorted list L correspond to dominant taxa when the list L is sorted in the increasing order of the abundance values, and the one or more top ranked entries in the sorted list L correspond to dominant taxa, and the one or more bottom ranked entries in the sorted list L correspond to sparse taxa when the list L is sorted in the decreasing order of the abundance values. Further, in step (c), counting minimum number of sparse taxa ($ST_i$) whose cumulative abundance is ≥i % of the total population count 'M', wherein the abundance values are progressively cumulated in order of increasing rank of each microbe in the sorted list L when the list L is sorted in the increasing order, or counting minimum number of sparse taxa ($ST_i$) whose cumulative abundance is ≥i % of the total population count 'M' wherein the abundance values are progressively cumulated in a decreasing rank of each microbe in the sorted list L when the list L is sorted in the decreasing order, and wherein 'i' is an integer or a fractional number. Further, in step (d), counting minimum number of dominant taxa ($DT_j$) whose cumulative abundance is ≥j % of the total population count 'M', wherein the abundance values are progressively cumulated in order of decreasing rank of each microbe in the sorted list L when the list L is sorted in the increasing order, or counting minimum number of dominant taxa ($DT_j$) whose cumulative abundance is ≥j % of the total population count 'M' wherein the abundance values are progressively cumulated in an increasing rank of each microbe in the sorted list L when the list L is sorted in the decreasing order, and wherein 'j' is an integer or a fractional number. Further, in step (e), repeating the steps (c) and (d) to obtain counts of $ST_i$ and $DT_j$ for a predefined range of values of i and j to generate two sets of values ST and DT respectively, wherein i and j belong to two identical arithmetic progressions within the predefined range, and wherein a common difference between consecutive terms of the arithmetic progression is a predefined integer or a predefined fractional value. Further, in step (f), computing a Cartesian product of the sets DT and ST to obtain a set C containing a plurality of ordered pairs corresponding to $DT_j$ and $ST_i$ values. Further in step (g), deriving a set DSR by computing ($DT_j \div ST_i$) for each ordered pair in the set C. Further, in step (h), computing the distribution characteristic value of the set 'DSR', wherein the distribution characteristic value of the set 'DSR' comprises a central tendency value of the set DSR. Further, in step (i), computing the 'taxonomic composition skew' value by applying a mathematical transformation on the distribution characteristic value comprising the central tendency value of the set DSR. The program further comprises a program code for determining the risk of the preterm delivery for the pregnant subject based on at least one of the central tendency value of the set DSR, the distribution characteristic value of the set DSR, or the taxonomic composition skew value.

The program further comprises a program code for generating the microbial taxonomic abundance profile for the microbiome sample by computationally analyzing, by the hardware processor, sequenced microbial DNA data using one or more taxonomic classification techniques. The sequenced microbial DNA data is obtained from the microbiome sample using a sequencing platform 112. The program further comprises a program code for generating the microbial taxonomic abundance profile for the microbiome sample by computationally analyzing, by the hardware processor, microbiome characterization data using one or more taxonomic classification techniques, wherein the microbiome characterization data is obtained from the microbiome sample. The microbiome characterization data is obtained from the microbiome sample by applying at least technique on the microbiome sample, wherein the at least one technique is selected from a group of techniques comprising a sequencing technique, a microscopic examination, a flow cytometry method, an in-vitro culture based method, one or more enzymatic or fluorescence assays, or one or more assays involving spectroscopic identification and screening of signals from complex microbial populations. The microbiome characterization data comprises sequenced microbial nucleic acid data, a Microscopic imaging data, a Flow cytometric cellular measurement data, a colony count and cellular phenotypic data of microbes grown in in-vitro cultures, and a signal intensity data.

BRIEF DESCRIPTION OF THE DRAWINGS

It should be appreciated by the skilled in the art that any block diagram herein represent conceptual views of illustrative systems and methods embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

The embodiments mentioned herein will be better understood from the following detailed description with reference to the drawings, in which:

FIGS. 5-a and 5-b illustrate a method for computation of taxonomic composition skew (TCS) value from abundance values of each of the plurality of microbes present in a microbiome sample of the pregnant subject, to further determine the risk of preterm delivery for the pregnant subject, in accordance with an embodiment of the present disclosure.

DETAILED DESCRIPTION OF EMBODIMENTS

Figure 1:
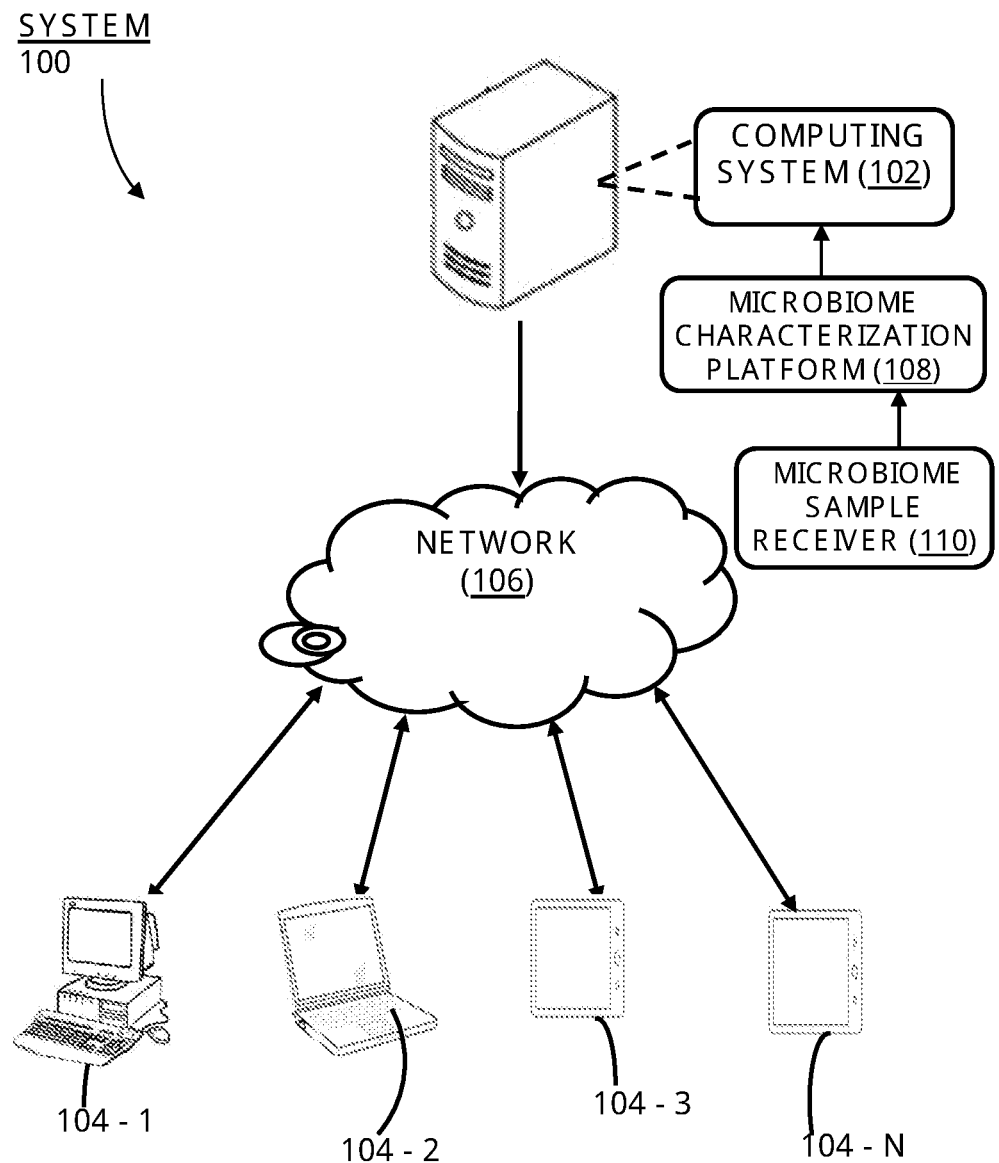
FIG. 1 illustrates a network implementation of the system for assessing a risk of preterm delivery of a pregnant subject in accordance with an embodiment of the present disclosure.

The embodiments stated herein and the various features and advantageous details thereof are explained in detail with reference to non-limiting embodiments that are illustrated in accompanying drawings and detailed in following description. The examples used herein are intended merely to facilitate an understanding of ways in which the embodiments described herein may be practiced and to further enable those of skilled in the art to practice the embodiments described herein. Accordingly, the examples should not be construed as limiting the scope of the embodiments described herein.

According to an embodiment, a system and a method for an assessment of a risk of a preterm delivery (PTD) of a pregnant subject is disclosed. In one aspect, the system and method for a qualitative and quantitative assessment of the risk of the preterm delivery (PTD) of a pregnant woman is disclosed. More particularly, the system and method to assess the risk of PTD by analyzing a microbiome sample obtained from the pregnant subject within the first 15 weeks of pregnancy or within the first trimester of pregnancy is disclosed. The system generates a microbial taxonomic abundance profile for the microbiome sample. The microbiome sample is obtained from the pregnant subject, and the microbial taxonomic abundance profile contains abundance values of each of a plurality of microbes identified to be present in the microbiome sample. The system further computes a distribution characteristic value such as a central tendency value of a set DSR and a 'Taxonomic Composition Skew' value of the set DSR, wherein the set DSR comprises values that quantify biases in the abundance values (represented in the form of the microbial taxonomic abundance profile) corresponding to the plurality of microbes present in the microbiome sample. Further, the system determines the risk of the preterm delivery for the pregnant subject based on the at least one of the distribution characteristic value, or the taxonomic composition skew value so computed. The system and method provides an early risk assessment procedure to accurately and reliably predict the risk of preterm delivery in the pregnant subject based on analysis of the microbiome sample collected from the pregnant subject within first 15 weeks of pregnancy or within the first trimester of pregnancy. Thus, risk assessment achieved from the presently disclosed method and system enables the pregnant subject to take precautionary or corrective medical advice or preventive procedures well in time to either reduce or obviate the risk of preterm delivery.

In accordance with the present disclosure, some of the objectives of the present disclosure are illustrated. A primary objective is to provide a method and system for early risk assessment for the preterm delivery outcome of the pregnant subject. In one embodiment, the pregnant subject is a pregnant woman. More particularly, to provide accurate risk assessment for the preterm delivery outcome of the pregnant subject in the earliest possible stage of pregnancy for e.g. the first trimester of pregnancy when the pregnant subject is a pregnant woman.

Another objective of the present disclosure is to provide the method and system for early risk assessment of the preterm delivery for the pregnant subject by quantifying diversity of microbes in a microbiome sample obtained from the pregnant subject. More particularly, the objective of the present disclosure is early risk assessment for preterm delivery in the pregnant subject by quantifying biases in abundance values of a plurality of microbes from a microbial taxonomic abundance profile corresponding to the microbiome sample obtained from the pregnant subject.

Another objective of the present disclosure is to provide an early diagnostic procedure which can accurately and reliably predict the risk of preterm delivery in the pregnant subject based on the microbiome sample collected from the pregnant subject within the first 15 weeks of pregnancy or within the first trimester of pregnancy, wherein the pregnant subject is a pregnant woman.

Another objective of the present disclosure is to assess the preterm delivery (PTD) risk of the pregnant subject by quantifying a taxonomic composition skew (TCS) value from the abundance values, represented in the form of a microbial taxonomic abundance profile, corresponding to the plurality of microbes present in the microbiome sample. The method and system employs the TCS value to perform a qualitative as well as quantitative assessment of the risk of the preterm delivery (PTD) outcome.

Another objective of the present disclosure is to assess the PTD risk for the pregnant subject by computing a distribution characteristic value, such as a central tendency value of a set DSR wherein the set DSR comprises values that quantify biases in the abundance values (represented in the form of a microbial taxonomic abundance profile) corresponding to the plurality of microbes present in the microbiome sample. The method and system employs the distribution characteristic value, such as the central tendency value of the set DSR to provide a qualitative as well as quantitative assessment of the risk of the preterm delivery (PTD) outcome.

Another objective of the present disclosure is to provide a method and system that predicts, within first 15 weeks of pregnancy or within the first trimester of pregnancy, the pre-disposition of the pregnant subject to a preterm delivery outcome, thereby enabling the pregnant subject to take precautionary or corrective medical advice or procedures that can potentially either reduce or obviate the risk of a preterm delivery outcome.

Other objectives and advantages of the present invention will be more apparent from the following description when read in conjunction with the accompanying figures, which are not intended to limit the scope of the present disclosure.

Figure 2:
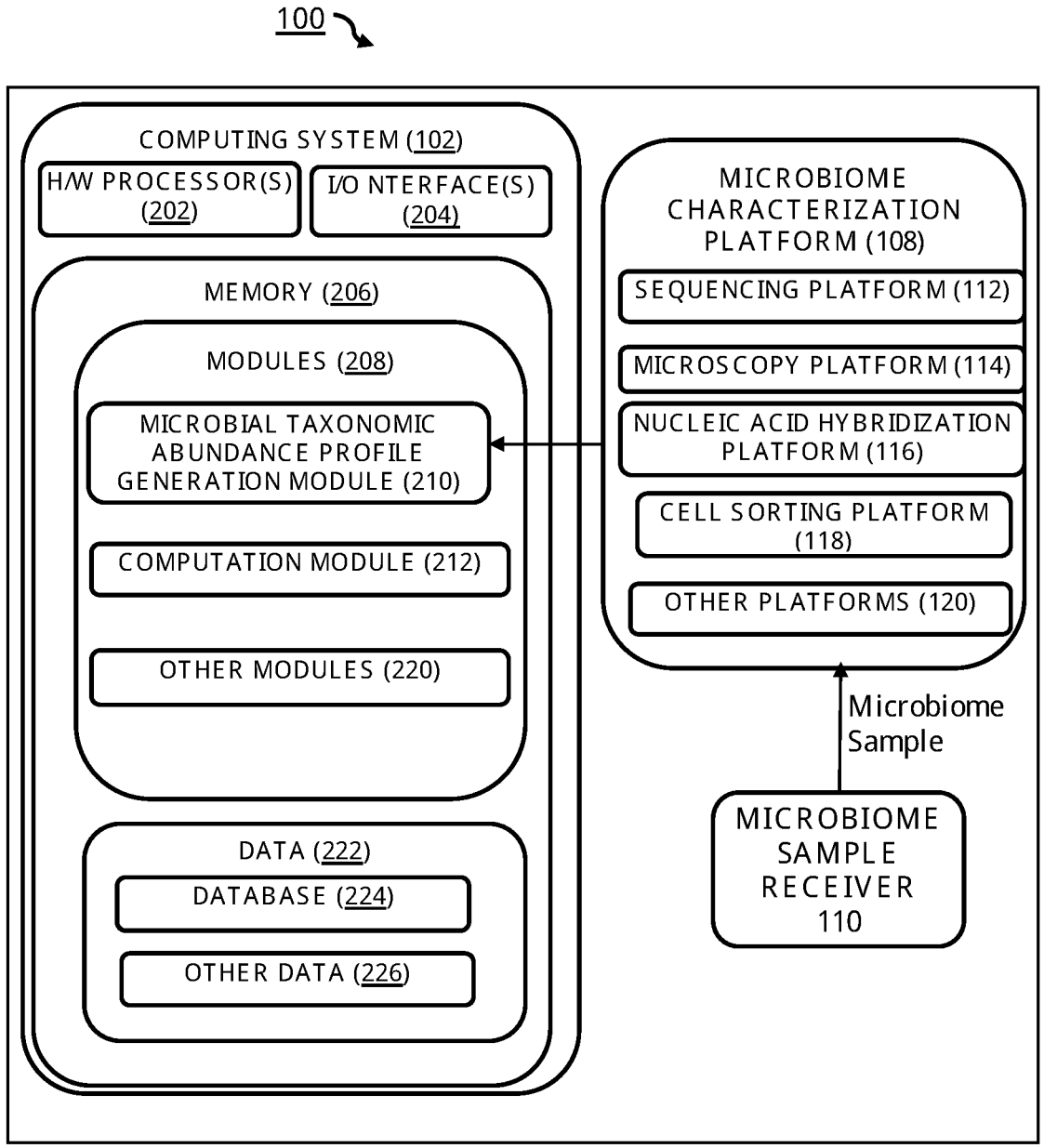
FIG. 2 illustrates the system for assessing the risk of preterm delivery of the pregnant subject in accordance with an embodiment of the present disclosure.

According to an embodiment of the present disclosure, referring to FIG. 1 and FIG. 2, a system 100 for assessing the risk of the preterm delivery (PTD) of the pregnant subject is described. There are shown preferred embodiments and these embodiments are described in the context of the following exemplary system and/or method.

It is however to be understood that the scope of protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (F PGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purpose of this description, a computer-usable or computer readable medium can be any apparatus that can comprise, store, communicate, propagate, or transport the program for use by or in connection with the instruction execution system, an apparatus, or a device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code includes at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

While aspects of described system and method may be implemented in any number of different computing systems, environments, and/or configurations, the embodiments are described in the context of the following exemplary system.

Referring to FIG. 1, a network implementation of the system 100 for assessing the risk of a preterm delivery (PTD) of the pregnant subject is illustrated, in accordance with an embodiment of the present subject matter. In one embodiment, system 100 is a combination of a computing system 102, a microbiome characterization platform 108, and a microbiome sample receiver 110.

The system 100 comprises the computing system 102, although, in one embodiment, the present subject matter is explained considering that the system 100 is implemented through the computing system 102, it may be understood that the computing system 102 may also be implemented as a variety of computing systems, such as a laptop computer, a desktop computer, a notebook, a workstation, a mainframe computer, a server, a network server, a tablet, a mobile phone, and the like. In one implementation, the computing system 102 may be implemented in a cloud-based environment. It will be understood that the computing system 102 may be accessed by multiple users through one or more user devices 104-1, 104-2 . . . 104-N, collectively referred to as user 104 hereinafter, or applications residing on the user devices 104. Examples of the user devices 104 may include but are not limited to, a portable computer, a personal digital assistant a handheld device, and a workstation. The user devices 104 are communicatively coupled to the computing system 102 through a network 106.

In one implementation, the network 106 may be a wireless network, a wired network or a combination thereof. The network 106 can be implemented as one of the different types of networks, such as intranet local area network (LAN), wide area network (WAN), the internet and the like. The network 106 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like to communicate with one another. Further the network 106 may include a variety of network devices, including routers, bridges, servers, computing devices, storage devices, and the like.

Referring now to FIG. 2, the computing system 102 is illustrated in accordance with an embodiment of the present subject matter. In one embodiment, the computing system 102 may include at least one hardware processor 202, an input/output (I/O) interface 204, and a memory 206. The at least one hardware processor 202 may be implemented as one or more microprocessors, microcomputers, microcontrollers, digital signal processors, central processing units, state machines, logic circuitries, and/or any devices that manipulate signals based on operational instructions. Among other capabilities, the at least one hardware processor 202 is configured to fetch and execute computer-readable instructions or modules 208 stored in the memory 206.

The I/O interface 204 may include a variety of software and hardware interfaces, for example, a web interface, a graphical user interface, and the like. The I/O interface 204 may allow the system 102 to interact with a user directly or through the client devices 104. Further, the I/O interface 204 may enable the computing system 102 to communicate with other computing devices, such as web servers and external data servers (not shown). The I/O interface 204 can facilitate multiple communications within a wide variety of networks and protocol types, including wired networks, for example, LAN, cable, etc., and wireless networks, such as WLAN, cellular, or satellite. The I/O interface 204 may include one or more ports for connecting a number of devices to one another or to another server.

The memory 206 may include any computer-readable medium or computer program product known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, a compact disks (CDs), digital versatile disc or digital video disc (DVDs) and magnetic tapes. The memory 206 may include modules 208 and data 222.

The modules 208 include routines, programs, programmed instructions, objects, components, data structures, etc., which perform particular tasks or implement particular abstract data types. In one implementation, the modules 208 may include a microbial taxonomic abundance profile generation module 210, a computation module 212, and other modules 220. The other modules 220 may include programs or coded instructions that supplement applications and functions of the computing system 102.

The data 222, amongst other things, serves as a repository for storing data processed, received, and generated by one or more of the modules 208 and the microbiome characterization platform 108. The data 222 may also include a database 224, and other data 226.

In one embodiment, the system 100 comprises the microbiome characterization platform 108 and the microbiome sample receiver 110. In one embodiment, the microbial taxonomic abundance profile generation module 210 is dynamically connected to the microbiome characterization platform 108. The microbiome characterization platform 108 may comprise at least one of a sequencing platform 112, a microscopy platform (114), a nucleic acid hybridization platform (116), a cell sorting platform (118) and other platforms (120). In one embodiment of the present disclosure, the microbiome characterization platform 108 receives the microbiome sample obtained from the pregnant subject via the microbiome sample receiver 110.

In one embodiment, in order to assess the risk of the preterm delivery (PTD) of the pregnant subject, the microbiome sample receiver 110 receives the microbiome sample obtained from the pregnant subject. In one aspect, the pregnant subject is a pregnant woman. In another aspect, the pregnant subject may be any female viviparous pregnant animal. In one aspect, wherein the pregnant subject is the pregnant woman, the microbiome sample may be obtained at any time point within first 15 weeks of pregnancy or within the first trimester of pregnancy. In another aspect, wherein the pregnant subject is the pregnant woman, the microbiome sample may be obtained within first 28 weeks of pregnancy from the pregnant woman. Still in another aspect, wherein the pregnant subject is a pregnant woman, the microbiome sample may be obtained within first 37 weeks of pregnancy from the pregnant woman. In another aspect, the microbiome sample may be collected from the pregnant subject at any time point during the entire gestation period for assessing the risk of PTD outcome. In one aspect, the microbiome sample is a vaginal swab sample of the pregnant subject. The microbiome sample is obtained from a mouth, skin, a gut, a vagina or any other body sites of the pregnant subject. The microbiome sample obtained from the pregnant subject may be at least one of a vaginal swab sample, a cervical mucus sample, a cervical swab sample, a vaginal swab including swab sample of a vaginal fornix, a urine sample, an amniotic fluid sample, a blood sample (whole blood sample), a serum sample, a plasma sample, a placental swab, an umbilical swab, a stool sample, a skin swab, an oral swab, a saliva sample, a periodontal swan, a throat swab, a nasal swab, a vesicle fluid sample, a nasopharyngeal swab, a nares swab, a conjunctival swab, a genital swab, a rectum swab, a tracheal aspirate, and a bronchial swab.

Further, in another embodiment, multiple microbiome samples may be collected at various time points during the entire gestation period from the pregnant subject. The preterm delivery is having the meaning as described in the available art. In general, by definition, preterm delivery is childbirth that occurs between the date of fetal viability and the end of the 37th week of gestation, wherein fetal viability is defined as the potential of the fetus to survive outside the uterus after birth, natural or induced. Fetal viability is usually placed at about seven months (28 completed weeks) of gestation, but in some cases, the fetal viability may occur earlier, even at 24 completed weeks of gestation. Premature birth gives less time for development of a baby in the womb.

In one embodiment of the present disclosure, the microbiome characterization platform (108) receives the microbiome sample from the microbiome sample receiver 110, and obtains microbiome characterization data from the microbiome sample. The microbiome characterization platform (108) obtains the microbiome characterization data from the microbiome sample by applying at least technique on the microbiome sample, wherein the at least one technique comprises a sequencing technique, a microscopic examination, a flow cytometry method, an in-vitro culture based method, one or more enzymatic or fluorescence assays, or one or more assays involving spectroscopic identification and screening of signals from complex microbial populations. The microbiome characterization data comprises sequenced microbial DNA data, a Microscopic imaging data, a Flow cytometric cellular measurement data, a colony count and cellular phenotypic data of microbes grown in in-vitro cultures, and a signal intensity data. One skilled in the art recognizes that there are numerous techniques available for obtaining the microbiome characterization data from the microbiome sample and hence not described in detail here.

The microbiome characterization platform (108) comprises at I east one of the sequencing platform (112), a microscopy platform (114), a nucleic acid hybridization platform (116), or a cell sorting platform (118) to obtain/generate the microbiome characterization data from the microbiome sample. A variety of microbiome characterization platforms are widely practiced and well established in the relevant field of research, hence not described in detail.

In one embodiment, the microbiome characterization platform (108) comprises the sequencing platform 112, and the sequencing platform 112 receives the microbiome sample from the microbiome sample receiver 110, wherein the microbiome sample is obtained from the pregnant subject. The sequencing platform 110 isolates microbial DNA corresponding to a plurality of microbes present in the microbiome sample using at least one DNA extraction technique. After isolating the microbial DNA, the sequencing platform 112 sequences the microbial DNA using at least one DNA sequencing technique to obtain sequenced microbial DNA data. The sequencing technique may be selected from the next-generation sequencing techniques. The next-generation sequencing techniques may comprise a Whole Genome Shotgun (WGS) sequencing technique, a fragment library based sequencing technique, a mate-pair library, a paired-end library based sequencing technique, or a combination thereof. One skilled in the art recognizes that there are numerous methods for DNA sequencing and are thus not described in detail here.

In one aspect, the sequencing platform 112, amplifies and sequences a bacterial 16S rRNA marker genes from the microbial DNA, wherein the microbial DNA are extracted from the microbiome sample. In another aspect, the sequencing platform 112, may amplify and sequence a bacterial 23S rRNA marker genes from the microbial DNA. The sequencing platform may sequence either full-length or specific variable regions of the bacterial 16S rRNA or 23S rRNA marker genes from the microbial DNA using the next-generation sequencing technique. Still, in another aspect, one or more phylogenetic marker genes other than or in addition to the bacterial 16S rRNA, and 23S rRNA marker genes may be amplified and sequenced from the microbial DNA. The sequencing platform 112 provides the sequenced microbial DNA data to the microbial taxonomic abundance profile generation module 210.

In another embodiment, the microscopy platform 114 may receive the microbiome sample obtained from the pregnant subject from the microbiome sample receiver 110. The microscopy platform 114 is used to perform automated or semi-automated microscopic examination or imaging, wherein a number and a type of microbial cells present in the received microbiome sample can be computed from the microscopic imaging data.

Still in another embodiment, the nucleic acid hybridization platform 116 may receive the microbiome sample obtained from the pregnant subject. The nucleic acid hybridization platform 116 receives the microbiome sample from the microbiome sample receiver 110. The nucleic acid hybridization platform 116 performs hybridization of short single stranded nucleic acid sequences derived from total microbial nucleic acid content present in the microbiome sample against an array of pre-synthesized nucleic acid sequence probes, which serves as markers for specific microbial taxonomic groups, wherein the hybridization events are captured and visualized using imaging techniques such as X-ray, Autoradiography or chromogenic methods, and wherein a number and type of microbial cells present in the microbiome sample can be computed from the imaging data.

Still in another embodiment, the cell sorting platform 118 may receive the microbiome sample obtained from the pregnant subject. The cell sorting platform 118 receives the microbiome sample from the microbiome sample receiver 110. The cell sorting platform 118 performs an in-vitro culture based method, one or more enzymatic or fluorescence assays, or one or more assays involving spectroscopic identification and screening of signals from complex microbial populations to obtain the microbiome characterization data such as a colony count and cellular phenotypic data of microbes grown in in-vitro cultures, and a signal intensity data.

Still in another embodiment, the other platforms 120 may receive the microbiome sample obtained from the pregnant subject. The other platforms 120 may execute one or more microbiome characterization techniques known to a person skilled in the art on the microbiome sample to obtain the microbiome characterization data. Still in another embodiment, the other platforms 120 may receive the microbiome sample obtained from the pregnant subject. The other platform executes one or more microbiome characterization techniques to obtain data from which number and type of microbial cells present in the received microbiome sample can be computed.

In another embodiment of the present disclosure, the microbial taxonomic abundance profile generation module 210 generates the microbial taxonomic abundance profile for the microbiome sample by analyzing the microbiome characterization data received from the microbiome characterization platform (108). The microbial taxonomic abundance profile generation module 210, computationally analyzes, by the hardware processor, the microbiome characterization data, using one or more taxonomic classification techniques to generate the microbial taxonomic abundance profile for the microbiome sample. The computation module 212 receives the microbial taxonomic abundance profile from the microbial taxonomic abundance profile generation module 210.

According to another embodiment of the present disclosure, the microbial taxonomic abundance profile generation module 210, computationally analyzes, by the hardware processor, the sequenced microbial DNA data using one or more taxonomic classification techniques to generate the microbial taxonomic abundance profile. The microbial taxonomic abundance profile comprises values indicating abundance of various individual taxonomic groups of plurality of microbes present in the sequenced microbial DNA data corresponding to the microbiome sample. The microbial taxonomic abundance profile contains abundance values of each of the plurality of microbes present in the microbiome sample. In one embodiment, the microbial taxonomic abundance profile is generated using assignment based taxonomic classification (binning) approaches. The assignment based taxonomic classification (binning) approaches may involve comparing sequences from the sequenced microbial DNA data and/or compositional level similarity of the sequenced microbial DNA data against existing reference sequence databases. In one example, the sequenced microbial DNA data corresponding to at least one of 16S rRNA marker genes, 23S rRNA marker genes, or any other phylogenetic marker genes may be computationally analyzed to generate the microbial taxonomic abundance profile by segregating the DNA sequences into Operational Taxonomic Units (OTUs), and the segregation into Operational Taxonomic Units (OTUs) is based on clustering of sequences. The clustering of sequences is further based on sequence level similarity of the Operational Taxonomic Units (OTUs).

In another embodiment, the sequenced microbial DNA data corresponding to either phylogenetic marker genes or Whole Genome Shotgun (WGS) sequence data of the microbial DNA corresponding to the plurality of microbes present in the microbiome sample may be computationally analyzed to generate the microbial taxonomic abundance profile by segregating or clustering the DNA sequences based on compositional similarity of the DNA sequences or by comparing the sequenced microbial DNA data against existing reference sequence databases. The computation module 212 receives the microbial taxonomic abundance profile from the microbial taxonomic abundance profile generation module 210.

After receiving the microbial taxonomic abundance profile, the computation module 212 computes a distribution characteristics value and Taxonomic Composition Skew value for the microbial taxonomic abundance profile. The 'Taxonomic Composition Skew' value and the distribution characteristic value quantify biases in the abundance values of the plurality of microbes from the microbial taxonomic abundance profile. The computation of the Taxonomic Composition Skew value and the distribution characteristic value is explained below.

In order to compute the 'Taxonomic Composition Skew' value and the distribution characteristic value for the microbial taxonomic abundance profile corresponding to the plurality of microbes present in the microbiome sample, in step (a), the computation module 212 obtains a total population count 'M' by computing a sum of the abundance values of the plurality of microbes from the microbial taxonomic abundance profile.

Further, in step (b), the computation module 212 creates a list L of various individual taxonomic groups (present in the microbiome sample) from the microbial taxonomic abundance profile. The list 'L' is created containing the abundance values of each of the plurality of microbes from the microbial taxonomic abundance profile. The individual taxonomic groups hereafter are referred to as taxon/taxa associated with each microbe from the microbiome sample. Further, in step b, the computation module 212 sorts the list 'L' containing the abundance values of the plurality of microbes from the microbial taxonomic abundance profile to create a sorted list L. The sorted list 'L' comprises of the abundance values of each of the plurality of microbes present in the microbial taxonomic abundance profile ranked in an increasing order or a decreasing order of the abundance values, thus the list L is sorted in the increasing order or in the decreasing order of the abundance values respectively. One or more top ranked entries in the sorted list L correspond to sparse taxa, and one or more bottom ranked entries in the sorted list L correspond to dominant taxa, when the list L is sorted in the increasing order of the abundance values. The one or more top ranked entries in the sorted list L correspond to dominant taxa, and the one or more bottom ranked entries in the sorted list L correspond to sparse taxa, when the list L is sorted in the decreasing order of the abundance values.

In step (c), the computation module 212 counts minimum number of sparse taxa $(ST_i)$ whose cumulative abundance is ≥i % of the total population count 'M', wherein the abundance values are progressively cumulated in order of increasing rank of each microbe in the sorted list L when the list L is sorted in the increasing order. Else, in step c, the computation module 212 counts minimum number of sparse taxa $(ST_i)$ whose cumulative abundance is ≥i % of the total population count 'M' wherein the abundance values are progressively cumulated in order of decreasing rank of each microbe in the sorted list L when the list L is sorted in the decreasing order. Herein, 'i' is an integer or a fractional number.

Further, in step (d), the computation module 212 counts minimum number of dominant taxa $(DT_j)$ whose cumulative abundance is ≥j % of the total population count 'M', wherein the abundance values are progressively cumulated in order of decreasing rank of each microbe in the sorted list L when the list L is sorted in the increasing order. Else, in step d, the computation module 216 counts minimum number of dominant taxa ($DT_j$) whose cumulative abundance is ≥j % of the total population count 'M' wherein the abundance values are progressively cumulated in order of increasing rank of each microbe in the sorted list L when the list L is sorted in the decreasing order. Herein, 'i' is an integer or a fractional number.

Further, in step (e), the computation module 212 repeatedly executes the steps c and d as explained above to obtain counts of $ST_i$ and $DT_j$ for a predefined range of values of i and j to generate two sets of values ST and DT respectively. Herein, i and j belong to two identical arithmetic progressions within the predefined range, and wherein a common difference between consecutive terms of the arithmetic progression is a predefined integer or a predefined fractional value. In one example, the sets ST and DT are shown below in equation (1) and (2) respectively.

$$ST=\{ST_1, ST_2, ST_3, \ldots ST_{50}\} \quad \text{Equation (1)}$$

wherein by definition, $ST_i$ are non-zero integers, and $ST_{(i+1)} \geq ST_i$, and 'i' varies in a range of 1 to 50 (such that 0<i≤50).

$$DT=\{DT_1, DT_2, DT_3, \ldots DT_{50}\} \quad \text{Equation (2)}$$

wherein by definition $DT_j$ are non-zero integers, and $DT_{(j+1)} \geq DT_j$, and 'j' varies in a range of 1 to 50 (such that 0<j≤50).

In one aspect, the predefined range of values of i and j lies in 0 to 50 (such that 0<i≤50 and 0<j≤50). In another aspect, the predefined range of values of i and j lies in a range of 0 to 100 (such that 0<i≤100 and 0<j≤100). The predefined range for i and j is defined such that i+j is equal to 100.

Further, in step (f), the computation module 212 computes a Cartesian product of the sets DT and ST to obtain a set C containing a plurality of ordered pairs corresponding to $DT_j$ and $ST_i$ values.

In one example, referring to the sets ST and DT from equations (1) and (2), the Cartesian product of the sets ST and DT are computed to obtain the set C. Thus, referring to the equations 1 and 2, and step (f), the set C contains 2500 couples (i.e. ordered-pairs) corresponding to $DT_j$ and $ST_i$ values, as shown in equation (3) below. In another embodiment, the number of ordered pairs in the Cartesian product of the sets ST and DT may depend on the sizes of the sets ST and DT.

$$C=DT \times ST=\{(DT_j, ST_i) | \text{ where } DT_j \in DT \text{ and } ST_i \in ST \text{ and 'i' and 'j' are positive integers} \leq 50\} \quad \text{Equation (3)}$$

In another embodiment, the difference between the cumulative abundances (computed while generating successive $ST_i$ and/or $DT_j$ values) may have any appropriate fractional or integer values other than 1. For example, in an alternate implementation, where the maximum value of i and j is 50, the set ST may contain 100 $ST_i$ values (where i=0.5, 1, 1.5, 2, ..., 50) and set DT may contain 100 $DT_j$ values (where j=0.5, 1, 1.5, 2, ..., 50). In another example, the number of ordered pairs in the Cartesian product of the sets ST and DT may be dependent on the sizes of the sets ST and DT.

Further, in step (g), the computation module 212 derives a set DSR based on the values $DT_j$ and $ST_i$ from the set C. In one embodiment, in step (g), the computation module 212 derives the set DSR by computing ($DT_j \div ST_i$) for each ordered pair in the set C. The set DSR is derived which comprises values obtained by computing ($DT_j \div ST_i$) for each ordered pair in the set C as shown in equation (4) below. Thus, the set DSR comprises values obtained by dividing $DT_j$ value by $ST_i$ value for each ordered pair in the set C as shown in the equation (4) below.

$$DSR=\{(DT_j \div ST_i) | \text{ where } (DT_j, ST_i) \in C, \text{ and 'i' and 'j' are positive integers} \leq 50\} \quad \text{Equation (4)}$$

Further, in step (h), the computation module 212 computes the distribution characteristic value of the set 'DSR'. The distribution characteristic value of the set 'DSR' comprises a central tendency value of the set DSR. The distribution characteristic value of the set DSR may comprise one of a maximum value of the set DSR, a minimum value of the set DSR, a variance of the set DSR, a skew of the set DSR, or a metric that characterizes modality, symmetry, and variability of distribution of values in the set DSR.

The computation module 212 computes a statistical measure, such as the central tendency value for the set 'DSR'. The central tendency value for the set 'DSR' is one of a mean, a median, a mode, or any statistical measure that identifies a single value as representative of an entire distribution of values in the set DSR.

The computation module 212 computes the 'taxonomic composition skew' value by applying a mathematical transformation on the distribution characteristic value. The computation module 212 computes the 'taxonomic composition skew' value by applying the mathematical transformation on the distribution characteristic value comprising the central tendency value of the set DSR. After computing the central tendency value, in step (i), the computation module 212 computes the 'taxonomic composition skew' (TCS) value by applying the mathematical transformation on the central tendency value of the set DSR. The mathematical transformation applied on the central tendency value comprises a subtraction of the central tendency value from 1 or computing an inverse of the central tendency value, or a mathematical transformation method that results in generating a higher numerical value of the taxonomic composition skew for a lower central tendency value and vice versa. The Taxonomic Composition Skew (TCS) value is computed using a following formula as shown in Equation (5) or Equation (6) below.

$$TCS=1-\text{central tendency value} \quad \text{Equation (5) or}$$

$$TCS=1/\text{central tendency value} \quad \text{Equation (6)}$$

In another exemplary embodiment, in the step (i), the computation module 212 computes the TCS value by using the distribution characteristic value of the set DSR. The computation module 212 computes the TCS value by applying a mathematical transformation on the distribution characteristic value of the set DSR. The distribution characteristic value of the set DSR may comprise a maximum value of the set DSR, a minimum value of the set DSR, a variance of the set DSR, a skew of the set DSR, or a metric that characterizes modality, symmetry, and variability of distribution of values in the set DSR.

In one exemplary embodiment, in case of a perfectly even distribution of the taxonomic groups in the microbiome sample, the value corresponding to ($DT_j \div ST_i$) can have a maximum value of 1. Consequently, the Taxonomic Composition Skew (TCS) value of any microbiome sample can vary in the range:

Taxonomic Composition Skew (TCS) value<1. The central tendency value of set DSR for any microbiome sample can vary in the range: 0≤central tendency value <1.

Further, the computation module 212, determines the risk of the preterm delivery for the pregnant subject based on at least one of the central tendency value of the set DSR, the distribution characteristic value of the set DSR or the taxonomic composition skew value. The computation module 212 further categorizes the pregnant subject into one or more risk categories for the preterm delivery based on at least one of the central tendency value of the set DSR, the distribution characteristic value of the set DSR or the Taxonomic Composition Skew value. The one or more risk categories comprises a low preterm delivery risk category, a moderate preterm delivery risk category and a high preterm delivery risk category.

In one example, when a vaginal microbiome sample is obtained from the pregnant woman, and when median of the set DSR is used as the central tendency value of the set DSR, as calculated in step h, and when the TCS value is generated by using the equation (5), and wherein preterm delivery risk categorization is based on the TCS value obtained based on the above said central tendency value of the set DSR, the low preterm delivery risk category is indicated for the taxonomic composition skew value greater than 0.922, the moderate preterm delivery risk category is indicated for the taxonomic composition skew value in a range of 0.887 to 0.922 (both values inclusive), and the high preterm delivery risk category is indicated for the taxonomic composition skew value less than or equal to 0.887.

In another embodiment, the preterm delivery risk categories for the pregnant subject may be indicated based on the central tendency value of the set DSR. The high preterm delivery risk category is indicated for the central tendency value of the set DSR greater than 0.113, the moderate preterm delivery risk category is indicated for the central tendency value of the set DSR in a range of 0.078 to 0.113 (both values inclusive), and the low preterm delivery risk category is indicated for the central tendency value of the set DSR less than 0.078, wherein the central tendency value of the set DSR is a median value of the set DSR, and wherein the microbiome sample obtained from the pregnant woman is a vaginal microbiome sample.

By way of an example, the procedure adopted for determining the above mentioned threshold values for various risk categories of the preterm delivery is described below. The following examples are provided by way of illustration only and not by way of limitation.

According to an exemplary embodiment, various steps involved in computation of the Taxonomic Composition skew value based on three hypothetical microbiome samples having almost similar sequencing coverage (Number of sequences: ~49350 in each sample) is illustrated below. The worked-out example illustrated below depict various steps employed for computing the Taxonomic Composition Skew value/metric by analyzing abundance values of various microbes in the microbiome sample obtained from the pregnant subject. The abundance values of the plurality of microbes have been represented in the form of a table (hereafter referred to as Microbial Taxonomic Abundance Profile). Table 1 (a-c) (below) depicts the Microbial Taxonomic Abundance Profiles for three microbiome samples.

TABLE 1

| a Sample 1 (S1) | | b Sample 2 (S2) | | c Sample 3 (S3) | |
|---|---|---|---|---|---|
| Taxon id | Abundance | Taxon id | Abundance | Taxon id | Abundance |
| 1 | 1 | 1 | 1 | 1 | 1 |
| 2 | 1 | 2 | 1 | 2 | 1 |
| 3 | 1 | 3 | 1 | 3 | 1 |

TABLE 1-continued

| a Sample 1 (S1) | | b Sample 2 (S2) | | c Sample 3 (S3) | |
|---|---|---|---|---|---|
| Taxon id | Abundance | Taxon id | Abundance | Taxon id | Abundance |
| 4 | 1 | 4 | 1 | 4 | 1 |
| 5 | 76 | 5 | 6 | 5 | 6 |
| 6 | 241 | 6 | 7 | 6 | 7 |
| 7 | 745 | 7 | 23 | 7 | 23 |
| 8 | 1027 | 8 | 56 | 8 | 56 |
| 9 | 2786 | 9 | 110 | 9 | 78 |
| 10 | 3598 | 10 | 2028 | 10 | 226 |
| 11 | 4863 | 11 | 3075 | 11 | 897 |
| 12 | 6721 | 12 | 7354 | 12 | 3954 |
| 13 | 7458 | 13 | 10326 | 13 | 9876 |
| 14 | 9852 | 14 | 12456 | 14 | 14725 |
| 15 | 11974 | 15 | 13879 | 15 | 19521 |
| $M_{(S1)}$ = 49345 | | $M_{(S2)}$ = 49324 | | $M_{(S3)}$ = 49373 | |

Table 1 (a-c) depicts Microbial taxonomic abundance profiles containing abundance values of various microbes (sorted in ascending order of the abundance of each microbe) present in three microbiome samples (S1-S3). Below each abundance profile, the value of M i.e. the total population count is also indicated. The value of M is obtained by computing a sum of the abundance values of the plurality of microbes from the microbial taxonomic abundance profile. It must be noted that the numeric value of abundance provided against each Taxon ID (microbe) represents the absolute count of DNA sequences in the sequenced microbiome sample assigned to that Taxon ID by the taxonomic classification technique employed.

Starting from the given Microbial Taxonomic Abundance Profile (as depicted in Table 1 a-c), the following steps are involved in the computation of Taxonomic Composition Skew value.

In Step 1, a total population count 'M' is obtained by computing a sum of the abundance values of the plurality of microbes from the microbial taxonomic abundance profile. Computation of M is illustrated in Table 1 a-c. Further, in Step 2, a sorted list 'L' containing the abundance values of each of the plurality of microbes from the microbial taxonomic abundance profile is created. The sorted list 'L' comprises of the abundance values of each of the plurality of microbes present in the microbial taxonomic abundance profile ranked in an increasing order or a decreasing order of the abundance values, and wherein, one or more top ranked entries in the sorted list L correspond to sparse taxa, and one or more bottom ranked entries in the sorted list L correspond to dominant taxa when the list L is sorted in the increasing order of the abundance values, and the one or more top ranked entries in the sorted list L correspond to dominant taxa, and the one or more bottom ranked entries in the sorted list L correspond to sparse taxa when the list L is sorted in the decreasing order of the abundance values. In the present example, the Sorted lists (L) for the 3 samples (S1, S2 and S3) indicated in Table 1 a-c are depicted below:

L(S1)={1, 1, 1, 1, 76, . . . , 9852, 11974}
L(S2)={1, 1, 1, 1, 6, . . . , 12456, 13879}
L(S3)={1, 1, 1, 1, 6, . . . , 14725, 19521}

In each of the sets depicted above, the corresponding list L is sorted in the increasing order of the abundance values of individual microbes in the respective microbiome sample. Consequently, one or more top ranked entries (i.e. beginning from the left hand side of the depicted lists) correspond to the sparse taxa, and one or more bottom ranked entries (i.e. beginning from the right hand side of the depicted lists)

correspond to the dominant taxa. Herein, the sparse taxa for L (S1) correspond to {1, 1, 1, 1, 76 . . . } and the dominant taxa for L (S1) correspond to { . . . , 9852, 11974}.

In step 3, minimum number of sparse taxa ($ST_i$) whose cumulative abundance is ≥i % of the total population count 'M' are counted, when the abundance values are progressively cumulated in order of an increasing order of the abundance value of each microbe in the sorted list L, when the list L is sorted in the increasing order.

In Step 3(*a*), considering a value of i=1, the minimum number of Sparse taxa ($ST_1$) which comprise ≥1% of the Total Population Count 'M' (wherein the sorted microbial abundances are cumulated in increasing order of the abundance value of each microbe) in each of the three microbiome samples is depicted below.

S1={1, 1, 1, 1, 76, 241, 745, 1027, 2786, 3598, 4863, 6721, 7458, 9852, 11974}.

In the above sample the cumulative abundance (1066) of the first 7 sparse taxa (highlighted in boldface fonts) i.e. comprises ≥1% of the Total Population Count (i.e. 49345). Consequently, $ST_1$ for S1=7.

Similarly, S2={1, 1, 1, 1, 6, 7, 23, 56, 110, 2028, 3075, 7354, 10326, 12456, 13879}. For S2, the cumulative abundance (2234) of the first 10 sparse taxa (highlighted in boldface fonts) comprises ≥1% of Total Population Count (i.e. 49324). Consequently, $ST_1$ for S2=10.

Similarly, S3={1, 1, 1, 1, 6, 7, 23, 56, 78, 226, 897, 3954, 9876, 14725, 19521}. For S3, the cumulative abundance (1297) of the first 11 sparse taxa (highlighted in boldface fonts) comprises ≥1% of Total Population Count (i.e. 49373). Consequently, $ST_1$ for S3=11.

In step 3(*b*), similarly, considering a value of i=2, the minimum number of Sparse taxa ($ST_2$) which comprise ≥2% of the Total Population Count 'M' (wherein the sorted microbial abundances are cumulated in increasing order of the abundance value of each microbe) in each of the three microbiome samples is depicted below.

S1={1, 1, 1, 1, 76, 241, 745, 1027, 2786, 3598, 4863, 6721, 7458, 9852, 11974}.

In the above sample the cumulative abundance (1066) of the first 7 sparse taxa (highlighted in boldface fonts) comprises ≥2% of Total Population Count (i.e. 49345). Consequently, $ST_2$ for S1=7.

Similarly, S2={1, 1, 1, 1, 6, 7, 23, 56, 110, 2028, 3075, 7354, 10326, 12456, 13879}. For S2, the cumulative abundance (2234) of the first 10 sparse taxa (highlighted in boldface fonts) comprises ≥2% of Total Population Count (i.e. 49324). Consequently, $ST_2$ for S2=10.

Similarly, S3={1, 1, 1, 1, 6, 7, 23, 56, 78, 226, 897, 3954, 9876, 14725, 19521}. For S3, the cumulative abundance (1297) of the first 11 sparse taxa (highlighted in boldface fonts) comprises ≥2% of Total Population Count (i.e. 49373). Consequently, $ST_2$ for S3=11.

In Step 3(*c*), similarly, considering a value of i=3, minimum number of Sparse taxa (ST3) which comprise ≥3% of the Total Population Count 'M' (wherein the sorted microbial abundances are cumulated in increasing order of the abundance value of each microbe) in each of the three microbiome samples is depicted below.

S1={1, 1, 1, 1, 76, 241, 745, 1027, 2786, 3598, 4863, 6721, 7458, 9852, 11974}. In the above sample, the cumulative abundance (1066) of the first 7 sparse taxa (highlighted in bold face fonts) comprises ≥3% of Total Population Count (i.e. 49345). Consequently, $ST_3$ for S1=7.

Similarly, S2={1, 1, 1, 1, 6, 7, 23, 56, 110, 2028, 3075, 7354, 10326, 12456, 13879}. For S2, the cumulative abundance (2234) of the first 10 sparse taxa (highlighted in boldface fonts) comprises ≥3% of Total Population Count (i.e. 49324). Consequently, $ST_3$ for S2=10.

Similarly, S3={1, 1, 1, 1, 6, 7, 23, 56, 78, 226, 897, 3954, 9876, 14725, 19521}. For S3, the cumulative abundance (5251) of the first 12 sparse taxa (highlighted in boldface fonts) comprises ≥3% of Total Population Count (i.e. 49373). Consequently, $ST_3$ for S3=12.

In Step 3(*d*), the steps 3*a*, 3*b*, and 3c are repeated to obtain, for each sample, counts of $ST_i$ wherein i comprises 50 integer values ranging from 1 to 50 (both 1 and 50 are included). This generates, for each sample, a set ($ST_{SampleName}$) comprised of 50 values each.

$ST_{SampleName}$={$ST_1, ST_2, ST_3, \ldots, ST_{50}$}

$ST_{S1}$={7, 7, 8, 8, 9, 9, 9, 9, 9, 10, 10, 10, 10, 10, 10, 10, 10, 11, 11, 11, 11, 11, 11, 11, 11, 11, 12, 12, 12, 12, 12, 12, 12, 12, 12, 12, 12, 13, 13, 13, 13, 13, 13, 13, 13, 13, 13}

$ST_{S2}$={10, 10, 10, 10, 11, 11, 11, 11, 11, 12, 12, 12, 12, 12, 12, 12, 12, 12, 12, 12, 12, 12, 12, 12, 12, 13, 13, 13, 13, 13, 13, 13, 13, 13, 13, 13, 13, 13, 13, 13, 13, 13, 13, 13, 13, 13, 14, 14, 14, 14}

$ST_{S3}$={11, 11, 12, 12, 12, 12, 12, 12, 12, 12, 13, 13, 13, 13, 13, 13, 13, 13, 13, 13, 13, 13, 13, 13, 13, 13, 14, 14, 14, 14, 14, 14, 14, 14, 14, 14, 14, 14, 14, 14, 14, 14, 14, 14, 14, 14, 14, 14, 14, 14}

Further, in Step 4, minimum number of dominant taxa ($DT_j$) whose cumulative abundance is ≥j % of the total population count 'M' are counted, when the abundance values are progressively cumulated in increasing rank of abundance value of each microbe in the sorted list L, when the list L is sorted in the increasing order.

Further, in Step 4(*a*), considering a value of j=1, the minimum number of Dominant taxa ($DT_1$) which comprise ≥1% of the Total Population Count 'M' (wherein the sorted microbial abundances are cumulated in increasing order of the abundance value of each microbe) in each of the three microbiome samples is depicted below.

S1={1, 1, 1, 1, 76, 241, 745, 1027, 2786, 3598, 4863, 6721, 7458, 9852, 11974}. In the above sample the cumulative abundance (11974) of the last 1 taxon (highlighted in boldface fonts) comprises ≥1% of Total Population Count (i.e. 49345). Consequently, $DT_1$ for S1=1.

Similarly, S2={1, 1, 1, 1, 6, 7, 23, 56, 110, 2028, 3075, 7354, 10326, 12456, 13879}. For S2, the cumulative abundance (13879) of the last 1 dominant taxon (highlighted in boldface fonts) comprises ≥1% of Total Population Count (i.e. 49324). Consequently, $DT_1$ for S2=1.

Similarly, S3={1, 1, 1, 1, 6, 7, 23, 56, 78, 226, 897, 3954, 9876, 14725, 19521}. For S3, the cumulative abundance (19521) of the last 1 dominant taxon (highlighted in boldface fonts) comprises ≥1% of Total Population Count (i.e. 49373). Consequently, $DT_1$ for S3=1.

Further, in Step 4(*b*), similarly, considering a value of j=2, the minimum number of Dominant taxa ($DT_2$) which comprise ≥2% of the Total Population Count 'M' (wherein the sorted microbial abundances are cumulated in increasing order of the abundance value of each microbe) in each of the three microbiome samples is depicted below.

S1={1, 1, 1, 1, 76, 241, 745, 1027, 2786, 3598, 4863, 6721, 7458, 9852, 11974}. In the above sample the cumulative abundance (11974) of the last 1 dominant taxon (highlighted in boldface fonts) comprises ≥2% of Total Population Count (i.e. 49345). Consequently, $DT_2$ for S1=1.

Similarly, S2={1, 1, 1, 1, 6, 7, 23, 56, 110, 2028, 3075, 7354, 10326, 12456, 13879}. For S2, the cumulative abundance (13879) of the last 1 dominant taxon (highlighted in bold face fonts) comprises ≥2% of Total Population Count (i.e. 49324). Consequently, $DT_2$ for S2=1.

Similarly, S3={1, 1, 1, 1, 6, 7, 23, 56, 78, 226, 897, 3954, 9876, 14725, 19521}. For S3, the cumulative abundance (19521) of the last 1 taxon (highlighted in boldface fonts) comprises ≥2% of Total Population Count (i.e. 49373). Consequently, $DT_2$ for S3=1

Further, in Step 4(c), the steps 4a and 4b are repeated to obtain, for each sample, counts of $DT_j$ wherein j comprises 50 integer values ranging from 1 to 50 (both 1 and 50 included). This computation generates, for each sample, a set ($DT_{SampleName}$) comprised of 50 values each.

$DT_{SampleName}$={$DT_1$, $DT_2$, $DT_3$, . . . , $DT_{50}$}

$DT_{S1}$={1, 1, 1, 1, 1, 1, 1, 1, 1, 1, 1, 1, 1, 1, 1, 1, 1, 1, 1, 1, 1, 1, 1, 2, 2, 2, 2, 2, 2, 2, 2, 2, 2, 2, 2, 2, 2, 2, 2, 2, 2, 2, 2, 2, 2, 3, 3, 3, 3, 3, 3}

$DT_{S2}$={1, 1, 1, 1, 1, 1, 1, 1, 1, 1, 1, 1, 1, 1, 1, 1, 1, 1, 1, 1, 1, 1, 1, 1, 1, 1, 1, 1, 2, 2, 2, 2, 2, 2, 2, 2, 2, 2, 2, 2, 2, 2, 2, 2, 2, 2, 2, 2, 2, 2}

$DT_{S3}$={1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 1, 2, 2, 2, 2, 2, 2, 2, 2}

Further, in Step 5, a Cartesian product of the sets DT and ST is computed to obtain a set C containing a plurality of ordered pairs corresponding to $DT_j$ and $ST_i$ values. For example, for sample S1, set $C_{S1}$ is obtained in the following manner.

$DT_{S1}$={1, 1, 1, 1, 1, 1, 1, 1, 1, 1, 1, 1, 1, 1, 1, 1, 1, 1, 1, 1, 1, 1, 1, 2, 2, 2, 2, 2, 2, 2, 2, 2, 2, 2, 2, 2, 2, 2, 2, 2, 2, 2, 2, 2, 2, 3, 3, 3, 3, 3, 3}

$ST_{S1}$={7, 7, 8, 8, 9, 9, 9, 9, 9, 10, 10, 10, 10, 10, 10, 10, 10, 11, 11, 11, 11, 11, 11, 11, 11, 11, 12, 12, 12, 12, 12, 12, 12, 12, 12, 12, 12, 12, 12, 13, 13, 13, 13, 13, 13, 13, 13, 13, 13}

$C_{S1}$=Cartesian product of sets $DT_{S1}$ and $ST_{S1}$ The Cartesian product set $C_{S1}$ is shown below in Table 2.

|  | $DT_1$ | $DT_2$ | $DT_3$ | $DT_4$ | $DT_5$ | $DT_6$ | $DT_7$ | $DT_8$ | . . . . . . | $DT_{50}$ |
|---|---|---|---|---|---|---|---|---|---|---|
| $ST_1$ | (1, 7) | (1, 7) | (1, 7) | (1, 7) | (1, 7) | (1, 7) | (1, 7) | (1, 7) | . . . . . . | (3, 7) |
| $ST_2$ | (1, 7) | (1, 7) | (1, 7) | (1, 7) | (1, 7) | (1, 7) | (1, 7) | (1, 7) | . . . . . . | (3, 7) |
| $ST_3$ | (1, 8) | (1, 8) | (1, 8) | (1, 8) | (1, 8) | (1, 8) | (1, 8) | (1, 8) | . . . . . . | (3, 8) |
| $ST_4$ | (1, 8) | (1, 8) | (1, 8) | (1, 8) | (1, 8) | (1, 8) | (1, 8) | (1, 8) | . . . . . . | (3, 8) |
| $ST_5$ | (1, 9) | (1, 9) | (1, 9) | (1, 9) | (1, 9) | (1, 9) | (1, 9) | (1, 9) | . . . . . . | (3, 9) |
| $ST_6$ | (1, 9) | (1, 9) | (1, 9) | (1, 9) | (1, 9) | (1, 9) | (1, 9) | (1, 9) | . . . . . . | (3, 9) |
| $ST_7$ | (1, 9) | (1, 9) | (1, 9) | (1, 9) | (1, 9) | (1, 9) | (1, 9) | (1, 9) | . . . . . . | (3, 9) |
| $ST_8$ | (1, 9) | (1, 9) | (1, 9) | (1, 9) | (1, 9) | (1, 9) | (1, 9) | (1, 9) | . . . . . . | (3, 9) |
| . . . | . . . | . . . | . . . | . . . | . . . | . . . | . . . | . . . | . . . . . . | . . . |
| . . . | . . . | . . . | . . . | . . . | . . . | . . . | . . . | . . . | . . . . . . | . . . |
| $ST_{50}$ | (1, 13) | (1, 13) | (1, 13) | (1, 13) | (1, 13) | (1, 13) | (1, 13) | (1, 13) | . . . . . . | (3, 13) |

In a similar way, set $C_{S2}$ and set $C_{S3}$ are obtained for Sample 2 and Sample 3 respectively. Further, in Step 6, for each sample, a set DSR is derived by computing ($DT_j \div ST_i$) for each ordered pair in the respective set $C_{S1}$, set $C_{S2}$ and set $C_{S3}$.

For example, for Sample 1, the set $DSR_{S1}$ (represented below in Table 3) is derived by computing ($DT_j \div ST_i$) for each ordered pair in the set $C_{S1}$.

TABLE 3 set $DSR_{S1}$

|  | $DT_1$ | $DT_2$ | $DT_3$ | $DT_4$ | $DT_5$ | $DT_6$ | $DT_7$ | $DT_8$ | . . . . . . | $DT_{50}$ |
|---|---|---|---|---|---|---|---|---|---|---|
| $ST_1$ | 0.1429 | 0.1429 | 0.1429 | 0.1429 | 0.1429 | 0.1429 | 0.1429 | 0.1429 | . . . . . . | 0.4286 |
| $ST_2$ | 0.1429 | 0.1429 | 0.1429 | 0.1429 | 0.1429 | 0.1429 | 0.1429 | 0.1429 | . . . . . . | 0.4286 |
| $ST_3$ | 0.1250 | 0.1250 | 0.1250 | 0.1250 | 0.1250 | 0.1250 | 0.1250 | 0.1250 | . . . . . . | 0.3750 |
| $ST_4$ | 0.1250 | 0.1250 | 0.1250 | 0.1250 | 0.1250 | 0.1250 | 0.1250 | 0.1250 | . . . . . . | 0.3750 |
| $ST_5$ | 0.1111 | 0.1111 | 0.1111 | 0.1111 | 0.1111 | 0.1111 | 0.1111 | 0.1111 | . . . . . . | 0.3333 |
| $ST_6$ | 0.1111 | 0.1111 | 0.1111 | 0.1111 | 0.1111 | 0.1111 | 0.1111 | 0.1111 | . . . . . . | 0.3333 |
| $ST_7$ | 0.1111 | 0.1111 | 0.1111 | 0.1111 | 0.1111 | 0.1111 | 0.1111 | 0.1111 | . . . . . . | 0.3333 |
| $ST_8$ | 0.1111 | 0.1111 | 0.1111 | 0.1111 | 0.1111 | 0.1111 | 0.1111 | 0.1111 | . . . . . . | 0.3333 |
| . . . | . . . | . . . | . . . | . . . | . . . | . . . | . . . | . . . | . . . . . . | . . . |
| . . . | . . . | . . . | . . . | . . . | . . . | . . . | . . . | . . . | . . . . . . | . . . |
| $ST_{50}$ | 0.0769 | 0.0769 | 0.0769 | 0.0769 | 0.0769 | 0.0769 | 0.0769 | 0.0769 | . . . . . . | 0.2308 |

In a similar way, set $DSR_{S2}$ and set $DSR_{S3}$ are derived by computing $(DT_j \div ST_i)$ for each ordered pair in set $C_{S2}$ and set $C_{S3}$ (corresponding to Sample 2 and Sample 3 respectively).

Further, in step 7, the central tendency value (or the distribution characteristic value) for the set 'DSR' is computed for each individual sample. In this example, median of the set DSR has been considered as the central tendency value of the set DSR.

Central tendency (Median) value of set $DSR_{S1}$=0.1538
Central tendency (Median) value of set $DSR_{S2}$=0.0909
Central tendency (Median) value of set $DSR_{S3}$=0.0769

Further, in Step 8, the 'Taxonomic Composition Skew' (TCS) value is computed by applying a mathematical transformation on the central tendency value. In this example, the mathematical transformation step comprises subtraction of the central tendency value from 1 (i.e. unity).

TCS=1−Central tendency value of (set DSR)
TCS value/metric for sample S1=1−median (set $DSR_{S1}$)=1−0.1538=0.8461.
TCS value/metric for sample S2=1−median ($DSR_{S2}$)=1−0.0909=0.909
TCS value/metric for sample S3=1−median ($DSR_{S3}$)=1−0.0769=0.932

The Table 4 (below) depicts the values of Central tendency value of set DSR (median of set DSR), 'Taxonomic Composition Skew' (TCS) value computed using Microbial taxonomic abundance profiles of three samples S1, S2, and S3 depicted in Table 4.

TABLE 4

Central Tendency Value (Median (DSR)) and Taxonomic Composition Skew for samples S1, S2 and S3.

| Sample Name | Central Tendency Value i.e. Median (DSR) | Taxonomic Composition Skew value (TCS) metric |
|---|---|---|
| S1 | 0.1538 | 0.8461 |
| S2 | 0.0909 | 0.909 |
| S3 | 0.0769 | 0.932 |

Further, in the step 9, it is to be noted that the predetermined preterm birth risk categorization thresholds are as follows—

High-PTD risk: Central Tendency Value (Median (DSR))>0.113;
Moderate-PTD risk: 0.078<=Central Tendency Value (Median(DSR))<=0.113; and
Low-PTD risk: Central Tendency Value (Median (DSR))<0.078.

High-PTD risk: Taxonomic Composition Skew (TCS) value<0.887;
Moderate-PTD risk: 0.887<=Taxonomic Composition Skew (TCS) value<=0.922; and
Low-PTD risk: Taxonomic Composition Skew (TCS)>0.922.

Hence, after applying these risk categories, for the 3 samples as analyzed in the above example can be categorized as follows—

Sample S1→High-PTD risk
Sample S2→Moderate-PTD risk
Sample S3→Low-PTD risk

Efficiency of the TCS value as a metric in application to determine the risk of the preterm delivery outcome is evaluated as demonstrated below. Furthermore, in an exemplary embodiment, a Cross Validation Strategy may be employed for evaluating an efficiency of the Taxonomic Composition Skew (TCS) value in predicting the preterm delivery (case) and the term delivery (control) outcome using the vaginal microbiome samples of pregnant women (sampled within 15 weeks of pregnancy). This exemplary embodiment may further be employed to determine the different preterm birth risk categorization thresholds of the TCS value as a metric.

Several diversity/inequality metric values are computed for microbiome samples corresponding to the pregnant subjects/women with a known/recorded delivery outcome. Delivery outcomes predicted based on a given diversity/inequality metric are compared against the known/recorded delivery outcomes to evaluate the efficiency of prediction. For a given diversity/inequality metric, Matthews Correlation Coefficient (MCC) is a measure that captures both specificity and the sensitivity of a metric for prediction of the delivery outcome. A perfect MCC value of +1 indicates complete segregation of the values of the diversity/inequality metric corresponding to microbiome samples obtained from the pregnant subjects whose pregnancy proceeded to a recorded preterm delivery outcome and microbiome samples obtained from the pregnant subjects whose pregnancy proceeded to a recorded term delivery outcome (i.e. a normal full-term gestation). Furthermore, referring to FIG. 3, Extent of Segregation (ES) values indicate the extent of segregation between the two sets of values $D_{TD}$ and $D_{PTD}$, wherein $D_{TD}$ represents the range of values calculated for given diversity metric from samples corresponding to the pregnant subjects with a known/recorded term delivery outcome, and wherein $D_{PTD}$ represents the range of values calculated for a given diversity metric from samples corresponding to the pregnant subjects with a known/recorded preterm delivery outcome(s), in accordance with an exemplary embodiment of the present disclosure. A higher ES value indicated a better segregation between the sets of values. The Taxonomic Composition Skew (TCS) value is observed to obtain perfect MCC values of +1 (for example in every week until the 15th week of pregnancy). It may therefore be assumed that a single vaginal microbiome sample obtained from a pregnant subject (pregnant woman) at any time point in pregnancy on or before the 15th gestation week can be employed for accurately predicting the risk of a preterm delivery (PTD) outcome using the TCS value as a metric.

The validation study is performed on a subset of vaginal microbiome samples (n=211) taken from a data corpus. The data corpus is derived as described herein. Publicly available vaginal microbiome sample data from three previously published studies is used for present evaluation. In each study, the number of samples corresponding to term and preterm delivery outcomes are indicated below in Table 5.

TABLE 5

Number of samples corresponding to the term delivery and preterm delivery outcomes

| Study | Total No. of Samples | No. of Term Samples | No. of Preterm Samples | Reference (DOI) |
|---|---|---|---|---|
| Study 1 | 208 | 165 | 43 | Romero et al., Microbiome, February 2014 (DOI: 10.1186/2049-2618-2-4) |
| Study 2 | 139 | 139 | — | Romero et al., Microbiome, May 2014 (DOI: 10.1186/2049-2618-2-18) |

TABLE 5-continued

Number of samples corresponding to the term delivery and preterm delivery outcomes

| Study | Total No. of Samples | No. of Term Samples | No. of Preterm Samples | Reference (DOI) |
|---|---|---|---|---|
| Study 3 | 698 | 517 | 181 | DiGiulio et al., PNAS, September 2015 (DOI: 10.1073/pnas.1502875112) |

The Operational Taxonomic Unit (OTU) level of taxonomic profiles (corresponding to Greengenes OTUs version 13.5) for the above mentioned vaginal microbiome sample data is obtained. Data corresponding to a total of 1045 samples, each of which had a minimum of 500 taxonomically assigned sequences, is analyzed during the overall evaluation process. Taxonomic composition skew (TCS) value for each of the 1045 microbiome samples is computed. In addition to TCS value, the following established and widely used ecological-diversity indices, viz., Shannon, Simpson, and Chao, denoting species diversity, evenness, and richness respectively, are also computed for the available microbiomes samples. Statistical measures used for ascertaining economic-inequality viz., Gini-coefficient, Ricci-Schutz, Atkinson, Theil, and Decile ratio (90:10) are also computed to check if these indices could also capture the skew in taxonomic composition distribution.

The available microbiome samples are segregated into 33 week-wise groups.

Group 'Week N' comprises of the vaginal microbiomes that are sampled at any time-point within the $N^{th}$ week of pregnancy (N ranging between 8-40). Microbiome samples in each group are labelled as 'Term delivery' or 'Preterm delivery' denoting reported 'full-term' or 'preterm' delivery outcome respectively. For each group, the diagnostic value/ability of individual indices to differentiate between the term delivery and the preterm delivery is estimated in terms of Matthews Correlation Coefficient (MCC). Matthews Correlation Coefficient (MCC) is a measure that captures both specificity and sensitivity of prediction/classification using a selected threshold value, as shown in equation (6) below. The terms TP, TN, FP, FN as shown in equation 6 are typically used in calculation of sensitivity/specificity or similar measures used for quantifying prediction accuracy of a classification technique.

$$MCC = \frac{TP \times TN - FP \times FN}{\sqrt{(TP+FP)(TP+FN)(TN+FP)(TN+FN)}} \quad \text{Equation (6)}$$

Wherein, in Equation (6), TP, TN, FP, and FN represent the number of true-positive predictions, true-negative predictions, false-positive predictions, and false-negative predictions, respectively.

A perfect MCC value of +1 indicates complete separation between the microbiome samples corresponding to the preterm delivery and the term delivery. For each group, the diagnostic value/ability of individual indices to differentiate between the term delivery and preterm delivery is estimated by first computing Matthews Correlation Coefficient (MCC) values for different selected threshold values for a given index and subsequently selecting a threshold value at which the maximum MCC value is obtained. In cases where a selected threshold value for a given index (diversity or an inequality measure) could completely differentiate/segregate between the microbiome samples corresponding to the term delivery and the preterm delivery (i.e. MCC=+1), the extent of segregation (ES) is further evaluated. A higher ES value indicates better separation between the two groups of microbiome samples that is the term delivery samples and the preterm delivery samples.

Figure 3:
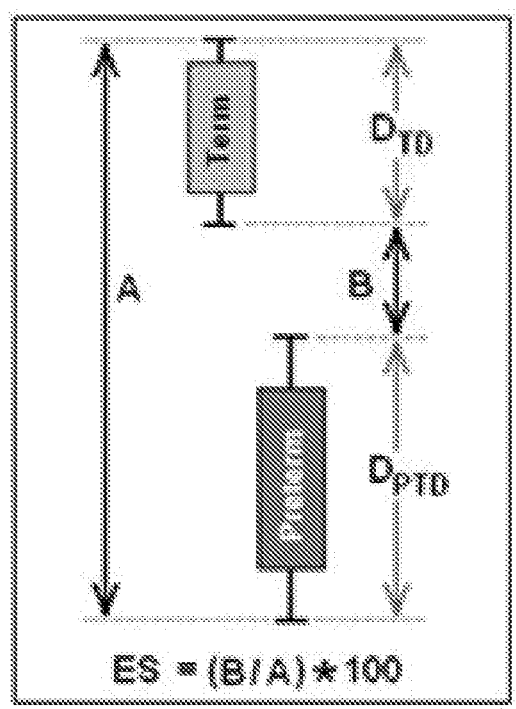
FIG. 3 illustrates a formula for computing Extent of Segregation (ES) for a given set of values for a given diversity metric, in accordance with an embodiment of the present disclosure.

Referring to FIG. 3, the extent of Segregation (ES) is an additional feature diagrammatically depicted, that can quantify a differentiating capability of an ecological-diversity/economic-inequality metric. The Extent of Segregation (ES) is computed by using equation 7 and 8 as depicted below.

$$\text{Extent of Segregation}(ES) = \frac{\min[\delta(\max D_{TD}, \min D_{PTD}), \delta(\max D_{PTD}, \min D_{TD})]}{\max[\delta(\max D_{TD}, \min D_{PTD}), \delta(\max D_{PTD}, \min D_{TD})]} \quad \text{Equation (7)}$$

$$\text{Extent of Segregation}(ES) = \frac{B}{A} \times 100 \quad \text{Equation (8)}$$

Wherein, in equation 7, $D_{TD}$ represents the set of values calculated for a given diversity/inequality metric for all samples corresponding to term delivery outcomes. $D_{PTD}$ represents the set of values calculated for a given diversity/inequality metric for all samples corresponding to preterm delivery outcomes. $\delta(\max D\_TD, \min D\_PTD)$ represents the absolute difference between the maximum value of the set D.sub.TD and the minimum value of the set $D_{PTD}$. $\delta(\max D\_PTD, \min D\_TD)$ represents the absolute difference between the maximum value of the set $D_{PTD}$ and the minimum value of the set $D_{TD}$. Further, values of B and A can be referred from FIG. 3.

Given that a primary objective of the present disclosure is to provide a system and method for early risk assessment for the preterm delivery outcome of a pregnant woman, evaluation results obtained using samples corresponding to only the first 15 weeks of pregnancy are shown in Table 6. Table 6 provides a comparative evaluation of a utility of various diversity and inequality indices in predicting the preterm delivery outcomes from vaginal microbiomes of pregnant women in the first 15 weeks of pregnancy. The data subset as shown in Table 6 is comprised of only those vaginal microbiome samples those are obtained within 15 weeks of pregnancy. The samples are appropriately labeled 'Term' or 'Preterm' denoting (reported) 'full-term' or 'preterm' delivery outcome respectively.

In Table 6, a perfect MCC value of +1 indicates complete separation between the microbiome samples corresponding to case (preterm delivery) and control (term delivery). The number of samples indicated at each gestation week includes all vaginal microbiomes samples that are sampled at any time-point on or before the respective gestation week. In cases where a threshold diversity or inequality measure could completely differentiate/segregate between samples corresponding to the term delivery and preterm delivery outcomes (i.e. MCC=+1), the extent of segregation (ES) is further evaluated and has been indicated in brackets adjacent to MCC values. Higher ES values indicate better separation between the two groups of samples. At each gestation week, the best attained MCC and ES values are indicated in bold face font.

Results obtained as shown in Table 6 indicate significant differences in ecological-diversity/economic-inequality measures between vaginal microbiome samples, obtained from the pregnant women with the term delivery or preterm delivery outcomes. One or more indices are observed to obtain a perfect MCC value of +1 (i.e. complete separation between the term delivery and the preterm delivery associated samples using a selected threshold) with the microbiome samples collected within 15 weeks of pregnancy i.e. Week 8 to Week 15. Table 6 shows comparative evaluation of a utility of various diversity and inequality indices in predicting preterm delivery outcomes from vaginal microbiomes of pregnant women in the first 15 weeks of pregnancy. At each gestation week, the best attained MCC values are indicated in bold face font, and the ES values are indicated in brackets adjacent to the MCC values. The number of samples indicated at each gestation week includes the vaginal microbiome samples that are sampled at any time-point on or before the respective gestation week.

15th gestation week can be employed for accurately predicting the risk of a preterm delivery (PTD) outcome using the TCS value as a metric.

Repeated random sub-sampling cross validation experiments were performed to further evaluate the efficiency of TCS, as well as various diversity and inequality metrics in predicting the pregnancy outcome. These experiments were also used for determining preterm birth risk categorization thresholds for the TCS metric. For the cross validation experiment(s), two-third of the samples are randomly selected and the randomly selected samples are used as training set for determining a threshold for the TCS value that provides maximal separation (quantified in terms of

TABLE 6

Comparative evaluation of a utility of various diversity and inequality indices in predicting preterm delivery outcomes from vaginal microbiomes of pregnant women in the first 15 weeks of pregnancy

| Gestation Week | No. of evaluated Vaginal Microbiome Samples | | | Matthews Correlation Coefficient (MCC) obtained with various diversity/inequality measures | | | | | | | | |
|---|---|---|---|---|---|---|---|---|---|---|---|---|
| (Weeks) | Preterm | Term | Total | TCS | Shannon | Simpson | Chao1 | Gini coefficient | Ricci-Schutz | Atkinson | Theil | Decile ratio (90:10) |
| 8 | 11 | 17 | 28 | 1(24.28) | 0.929 | 0.856 | 1(15.40) | 0.856 | 0.699 | 0.551 | 0.804 | 0.718 |
| 9 | 16 | 29 | 45 | 1(21.96) | 0.953 | 0.812 | 1(9.24) | 0.905 | 0.658 | 0.612 | 0.858 | 0.626 |
| 10 | 22 | 41 | 63 | 1(8.39) | 0.966 | 0.797 | 1(4.36) | 0.897 | 0.720 | 0.660 | 0.863 | 0.540 |
| 11 | 29 | 64 | 93 | 1(7.64) | 0.926 | 0.721 | 1(2.89) | 0.925 | 0.773 | 0.749 | 0.904 | 0.532 |
| 12 | 39 | 87 | 126 | 1(1.68) | 0.871 | 0.719 | 0.964 | 0.890 | 0.776 | 0.720 | 0.871 | 0.518 |
| 13 | 50 | 105 | 155 | 1(1.68) | 0.868 | 0.690 | 0.971 | 0.883 | 0.779 | 0.732 | 0.869 | 0.542 |
| 14 | 61 | 133 | 194 | 1(1.68) | 0.822 | 0.635 | 0.976 | 0.882 | 0.771 | 0.720 | 0.870 | 0.548 |
| 15 | 62 | 149 | 211 | 1(1.68) | 0.817 | 0.635 | 0.977 | 0.887 | 0.780 | 0.731 | 0.875 | 0.563 |

Amongst the compared indices, Taxonomic Composition Skew (TCS) value as a metric as disclosed in the present disclosure is observed to outperform all other indices as shown in Table 6. Furthermore, TCS value is observed to obtain perfect MCC values of +1 (in every week until the 15th week of pregnancy), thereby indicating that a single microbiome sample, for example a vaginal microbiome sample, obtained from a pregnant woman at any time point in pregnancy on or before the 15.sup.th gestation week can be employed for accurately diagnosing or predicting the risk of a preterm delivery outcome in an effective and reliable way. More importantly, a comparison of ES (Extent of Segregation) values obtained for various metrics/indices (in cases wherein the MCC value of +1 is obtained) indicates that ES with TCS value is 5-9% higher than that obtained with the other compared metrics/indices. Higher ES values indicate a higher amount of confidence with respect to the differentiating capability of the metric/index. Although, in principle, the TCS value obtained from the taxonomic profile of an individual vaginal microbiome sample (obtained before 15th gestation week) can help in ascertaining the risk of preterm delivery, in real-world setting, wherever possible, it may be ideal to obtain multiple samples (e.g. weekly) from the same subject to ascertain preterm delivery risk prior to initiating any prophylactic, therapeutic, or counseling measures.

The TCS value is observed to obtain perfect MCC values of +1 (for example in every week until the 15th week of pregnancy). It may therefore be assumed that a single vaginal microbiome sample obtained from a subject (pregnant woman) at any time point in pregnancy on or before the MCC value) between the microbiome samples corresponding to the preterm (case) delivery and the term (control) delivery outcomes. The efficiency of so determined threshold is subsequently evaluated using the test set which comprised of remaining one-third of the microbiome samples. The above said procedure is iterated 1000 times. In each of the iterations, the efficiency of the threshold of the TCS value was evaluated in terms of six parameters viz. accuracy, sensitivity, specificity, positive predictive value (PPV), negative predictive value (NPV), and Matthews's correlation coefficient (MCC). Mean values of the six evaluation parameters across 1000 iterations are provided in Table 7 below. Table 7 also includes results of the same cross validation experiment(s) performed with other ecological-diversity/economic-inequality metrics consisting Shannon, Simpson, Chad, Gini coefficient, Ricci-Schutz, Atkinson, Theil, Decile Ratio.

Table 7 shows results of cross-validation experiments (with vaginal microbiome samples taken from pregnant women within 15 weeks of pregnancy) providing a comparison of the efficiency of the various evaluated metrics in terms of accuracy, sensitivity, specificity, positive predictive value (PPV), negative predictive values (NPV), and Matthews correlation coefficient (MCC). PPV=TP/(TP+FP); NPV=TN/(TN+FN); Accuracy=(TP+TN)/(TP+TN+FP+FN); Sensitivity=TP/(TP+FN); Specificity=TN/(TN+FP). Mean values of the six evaluation parameters across 1000 iterations of cross-validation with each metric are provided in the table 7 and the best attained values are indicated in bold-face font. The standard deviation values are indicated in brackets below the respective mean values. Values in the table 7 have been rounded to the second decimal place.

| Metric | Accuracy | Sensitivity | Specificity | Positive Predictive Value (PPV) | Negative Predictive Value (NPV) | Matthews Correlation Coefficient (MCC) |
|---|---|---|---|---|---|---|
| TCS | 1.00 | 0.99 | 1.00 | 0.99 | 1.00 | 0.99 |
|  | (0.01) | (0.03) | (0.01) | (0.02) | (0.01) | (0.02) |
| Shannon | 0.91 | 0.85 | 0.94 | 0.86 | 0.94 | 0.79 |
|  | (0.03) | (0.07) | (0.03) | (0.07) | (0.03) | (0.06) |
| Simpson | 0.84 | 0.52 | 0.98 | 0.91 | 0.83 | 0.60 |
|  | (0.04) | (0.09) | (0.02) | (0.08) | (0.04) | (0.08) |
| Chao1 | 0.98 | 0.96 | 0.98 | 0.96 | 0.98 | 0.95 |
|  | (0.02) | (0.04) | (0.02) | (0.05) | (0.02) | (0.04) |
| Gini coefficient | 0.94 | 0.84 | 0.98 | 0.95 | 0.94 | 0.85 |
|  | (0.02) | (0.07) | (0.03) | (0.07) | (0.03) | (0.06) |
| Ricci-Schutz | 0.90 | 0.72 | 0.97 | 0.91 | 0.89 | 0.74 |
|  | (0.03) | (0.09) | (0.03) | (0.09) | (0.04) | (0.07) |
| Atkinson | 0.87 | 0.69 | 0.94 | 0.84 | 0.88 | 0.68 |
|  | (0.03) | (0.10) | (0.05) | (0.11) | (0.04) | (0.08) |
| Theil | 0.93 | 0.81 | 0.98 | 0.95 | 0.93 | 0.83 |
|  | (0.03) | (0.08) | (0.04) | (0.08) | (0.03) | (0.07) |
| Decile Ratio (90:10) | 0.82 | 0.40 | 0.99 | 0.95 | 0.80 | 0.53 |
|  | (0.04) | (0.09) | (0.01) | (0.08) | (0.04) | (0.08) |

As evident from the data shown in Table 7, the TCS value used as a metric obtains significantly higher values of accuracy, sensitivity, specificity, PPV, and NPV which clearly indicates utility of the TCS value in accurately diagnosing/predicting the risk of the preterm delivery from a single vaginal microbiome sample taken within 15 weeks of pregnancy.

According to an exemplary embodiment, following procedure is adopted for defining the thresholds of the TCS values for preterm delivery risk-categorization. According to an example, in the cross validation experiments as described above, the mini mum and the maximum threshold values for the TCS value (metric), obtained from the 1000 randomly selected training sets, which provided the highest MCC values in each of the 1000 iterations, are identified as 0.887 and 0.922. These minimum and the maximum TCS threshold values are considered for defining three preterm delivery risk-categories. The categories are meant to provide a pregnant woman a qualitative assessment of the risk of a preterm delivery (PTD) outcome in a clinical setting. The categories are detailed below: TCS<0.887→High-PTD risk, 0.887<=TCS<=0.922→Moderate-PTD risk and TCS>0.922→-Low-PTD risk.

In another embodiment of the present disclosure, the preterm risk categorization module may utilize different sets of predefined risk categorization thresholds suitable for:
1) one or more microbiome samples collected at different time points during pregnancy,
2) one or more microbiome samples collected from body sites other than the vagina, and
3) one or more microbiome samples collected from subjects belonging to different geographies, ethnicities, or subjects assessed with various maternal risk factors for preterm delivery outcome. Such predefined risk categorization thresholds may be computed by analyzing microbiome data obtained from relevant cohorts.

According to an embodiment, one or more advantages of the present disclosure as described herein. However, the advantages of the present disclosure described herein do not limit to the advantages mentioned below.

In one embodiment, the system and method assesses the risk of preterm delivery outcome within 15 weeks of pregnancy or earlier than 15 weeks and accurately predict risk or predisposition to the preterm delivery with significantly high positive predictive value (PPV).

In another embodiment, the system and method assesses the risk of preterm delivery outcome anytime during pregnancy, and accurately predict risk or predisposition to the preterm delivery with significantly high positive predictive value (PPV).

The system and method enables determination of the risk of the preterm delivery for the pregnant subject based on at least one of a distribution characteristic value of the set DSR obtained from a microbial taxonomic abundance profile of the microbiome sample or the taxonomic composition skew value computed based on the microbial taxonomic abundance profile of the microbiome sample. The distribution characteristic value of the set DSR comprises a central tendency value of the set DSR.

The system and method enables determination of the risk of the preterm delivery for the pregnant subject based on at least one of the distribution characteristic value such as the central tendency value of the set DSR obtained from the microbial taxonomic abundance profile of the microbiome sample or the taxonomic composition skew value shows sufficient extent of segregation in prediction of term and preterm delivery of the pregnant subject, hence the central tendency value, the distribution characteristic value of the set DSR and the taxonomic composition skew has prediction accuracy and better differentiating capability in term delivery and preterm delivery of the pregnant subjects.

A high PPV obtained by the presently disclosed method and system significantly minimizes one or more chances of incorrectly categorizing the pregnant subject having a potential risk of the preterm delivery compared to the pregnant subject with no such risk of preterm delivery.

Further, presently disclosed system and method provides sufficient time for the pregnant woman/subject (detected with a risk of PTD outcome) to take required 'precautionary/corrective' medical advice or procedures that reduce or obviate the risk of PTD.

Being microbiome based method, the present disclosure is applicable even in cases of first pregnancies, or preterm outcomes which are not driven by vaginal infections or fetal or uterine abnormalities or previously known risk factors (e.g. a previous preterm delivery history).

The sampling method and system disclosed in present disclosure comprises of non-invasive sample collection techniques, hence presently disclosed method and system for assessing the preterm delivery risk is more comfortable to the pregnant subject. Further, a single sample is sufficient to make an accurate diagnosis in the presently disclosed method.

Furthermore, the system and method requires the sample to be obtained anytime within the first 15 weeks of pregnancy, and any discomfort experienced by the pregnant subjects due to the sampling procedure is significantly lower as compared to the sampling techniques employed by prior arts, which are in some cases invasive, and are typically applicable in later stages of pregnancy.

Some prior arts suggest bacterial vaginosis (BV) as a predisposing factor for PTD.

Consequently, some prior art methods involve monitoring an abundance or presence of specific bacterial pathogens in vaginal swabs for predicting predisposition to PTD.

Present disclosure indicates a prediction method involving study of microbiome sample obtained from the pregnant subject, but differs from such prior art in several respects. Present disclosure do not base prediction or assessment of PTD risk on mere abundance changes of specific bacterial pathogens. Presently disclosed system and method for assessing the risk of PTD outcome is based on characteristics of a community of microbes at a population level present in the microbiome sample (irrespective of whether or not the subject has BV).

The system and method for assessing the risk for preterm delivery outcome of the pregnant subject is tested and validated using publicly available vaginal microbiome data from the following publications as given herein including Romero et al., Microbiome, May 2014, Romero et al., Microbiome, February 2014, and D B DiGiulio et al., PNAS, September 2015.

Figure 4:
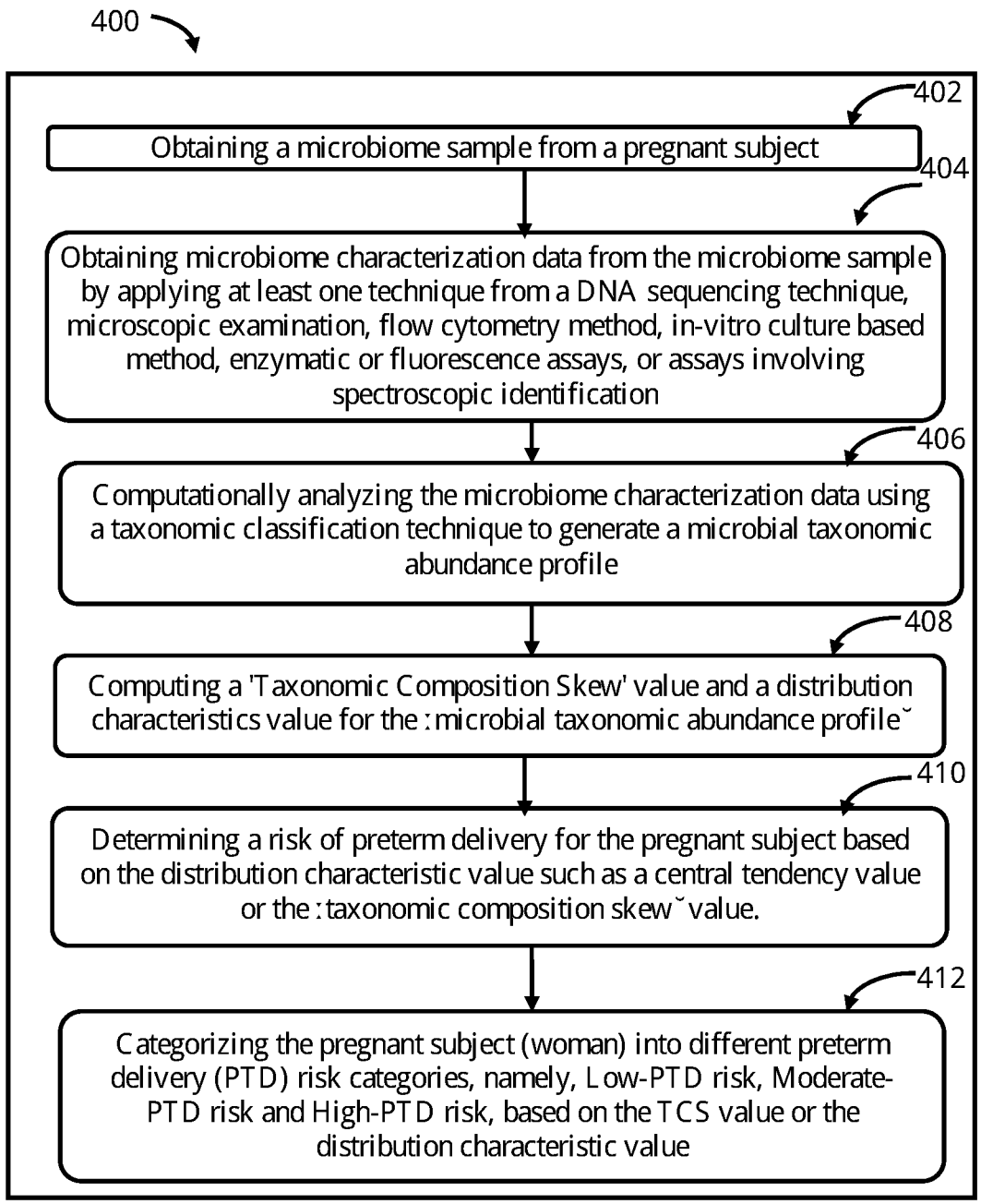
FIG. 4 illustrates a method for assessing a risk of preterm delivery outcome of a pregnant subject, in accordance with one embodiment of the present disclosure.

Referring now to FIG. 4, a method 400 for early risk assessment of a preterm delivery outcome of a pregnant subject is shown, in accordance with an embodiment of the present subject matter. The method 400 may be described in the general context of computer executable instructions. Generally, computer executable instructions can include routines, programs, objects, components, data structures, procedures, modules, functions, etc., that perform particular functions or implement particular abstract data types. The method 400 may also be practiced in a distributed computing environment where functions are performed by remote processing devices that are linked through a communications network. In a distributed computing environment, computer executable instructions may be located in both local and remote computer storage media, including memory storage devices.

The order in which the method 400 is described is not intended to be construed as a limitation, and any number of the described method blocks can be combined in any order to implement the method 400 or alternate methods. Additionally, individual blocks may be deleted from the method 400 without departing from the spirit and scope of the subject matter described herein. Furthermore, the method can be implemented in any suitable hardware, software, firmware, or combination thereof. However, for ease of explanation, in the embodiments described below, the method 400 may be considered to be implemented in the above described system 100.

At step 402, a microbiome sample from the pregnant subject may be obtained. The microbiome sample from the pregnant subject may be obtained within first 15 weeks of pregnancy or within a first trimester of the pregnancy or within a second trimester of the pregnancy, wherein the pregnant subject is a woman. In another aspect, the microbiome sample from the pregnant subject may be received within first 28 weeks of pregnancy or within first 37 weeks of pregnancy, wherein the pregnant subject is pregnant woman. The microbiome sample from the pregnant subject may be received at any time point during the pregnancy. In one embodiment, the pregnant subject is a pregnant woman. In another embodiment, the pregnant subject is a female viviparous animal. In another embodiment, the microbiome sample may be collected from a pregnant subject at any time point during the entire gestation period for assessing the risk of PTD outcome of the pregnant subject.

In one implementation, the microbiome sample receiver 110 may collect or receive the microbiome sample from the pregnant subject. The microbiome sample may be obtained from a mouth, skin, a gut, a vagina or other body sites of the pregnant subject. The microbiome sample is selected from a group comprising a vaginal swab sample, a cervical mucus sample, a cervical swab sample, a vaginal swab including swab sample of a fornix, a urine sample, an amniotic fluid sample, a blood sample, a serum sample, a plasma sample, a placental swab, an umbilical swab, a stool sample, a skin swab, an oral swab, a saliva sample, a periodontal swab, a throat swab, a nasal swab, a vesicle fluid sample, a nasopharyngeal swab, a nares swab, a conjunctival swab, a genital swab, a rectum swab, a tracheal aspirate, and a bronchial swab.

Further, in one embodiment, the method at step 404, comprise, obtaining, via microbiome characterization platform 108, microbiome characterization data of the microbiome sample. The microbiome characterization data is obtained by applying one or more techniques comprising a sequencing technique, a microscopic examination, a flow cytometry method, an in-vitro culture based method, one or more enzymatic or fluorescence assays, or one or more assays involving spectroscopic identification and screening of signals from complex microbial populations, and wherein the microbiome characterization data comprises sequenced microbial DNA data, a Microscopic imaging data, a Flow cytometry cellular measurement data, a colony count and cellular phenotypic data of microbes grown in in-vitro cultures, and a signal intensity data.

In one embodiment, after receiving the microbiome sample, at step 404, sequenced microbial DNA data is obtained via a sequencing platform 112 for the microbiome sample. Obtaining the sequenced microbial DNA data comprises isolating microbial DNA corresponding to the plurality of microbes present in the microbiome sample using at least one DNA extraction technique. In one implementation, the sequencing platform 106 isolates the microbial DNA corresponding to the plurality of microbes present in the microbiome sample using at least one DNA extraction technique.

Further, in step 404, the microbial DNA is sequenced using at least one DNA sequencing technique to obtain the sequenced microbial DNA data. In one implementation, the sequencing platform 112 sequences the microbial DNA using at least one DNA sequencing technique to obtain the sequenced microbial DNA data. In one aspect, bacterial 16S rRNA or 23S rRNA marker genes are amplified and sequenced from the microbial DNA. In another aspect, either a full-length or one or more specific regions of the bacterial 16S rRNA or 23S rRNA marker genes are amplified and sequenced from the microbial DNA. In one implementation, the sequencing platform 212 amplifies and sequences a bacterial 16S rRNA or 23S rRNA marker genes from the microbial DNA so extracted from the microbiome sample.

In one embodiment, one or more phylogenetic marker genes may be amplified and sequenced from the microbial DNA. The DNA sequencing technique may be selected from a next-generation sequencing techniques, wherein the next-generation sequencing techniques comprises a Whole Genome Shotgun (WGS) sequencing, a fragment library based sequencing technique, a mate-pair library or a paired-end library based sequencing technique, or a combination thereof.

Further, in one embodiment, after obtaining the microbiome characterization data, in step 406, the microbial taxonomic abundance profile for the microbiome sample may be generated by computationally analyzing, by the hardware processor, the microbiome characterization data, using one or more taxonomic classification techniques.

Still in another embodiment, in step 406, the microbial taxonomic abundance profile for the microbiome sample is generated by computationally analyzing, by the hardware processor, the sequenced microbial DNA data using one or more taxonomic classification techniques. The microbial taxonomic abundance profile comprises abundance values of various individual taxonomic groups present in the microbiome sample. In one implementation, the Microbial taxonomic abundance profile generation module 210, computationally analyzes, by the hardware processor, the sequenced microbial DNA data using the one or more taxonomic classification techniques to generate the microbial taxonomic abundance profile for the microbiome sample. In another aspect of the present disclosure, the microbial taxonomic abundance profile for the microbiome sample may be generated by analyzing the microbiome sample using one or more techniques comprising a microscopic examination, a flow cytometric methodology, an in-vitro culture based method, one or more enzymatic or fluorescence assays, or one or more assays involving spectroscopic identification and screening of signals from complex microbial populations.

After generating the microbial taxonomic abundance profile, in step 408, the microbial taxonomic abundance profile is received by the computation module 212. The microbial taxonomic abundance profile contains abundance values of each of the plurality of microbes present in the microbiome sample. Further, in step 408, a 'Taxonomic Composition Skew' value, and a distribution characteristics value for the microbial taxonomic abundance profile is computed. The 'Taxonomic Composition Skew' value, and the distribution characteristic value quantify biases in the abundance values of the plurality of microbes from the microbial taxonomic abundance profile. The computation of the Taxonomic Composition Skew value and the distribution characteristic value comprises following steps. The computation of the Taxonomic Composition Skew value and the distribution characteristics value, in the step 408 further comprises a plurality of steps as described below. Step 408 further comprises steps 502-518 as shown in FIG. 5-a and FIG. 5-b.

Referring to FIG. 5-a, and FIG. 5-b the steps 502-518 are explained herein. In step 502, a total population count 'M' is obtained by computing a sum of the abundance values of the plurality of microbes from the microbial taxonomic abundance profile. Further, in step 504, a sorted list 'L' containing the abundance values of the plurality of microbes from the microbial taxonomic abundance profile is created. The sorted list 'L' comprises of abundance values of each of the plurality of microbes present in the microbial taxonomic abundance profile ranked in an increasing order or a decreasing order of the abundance values. One or more top ranked entries in the sorted list L correspond to sparse taxa, and one or more bottom ranked entries in the sorted list L correspond to dominant taxa when the list L is sorted in the increasing order of the abundance values, and the one or more top ranked entries in the sorted list L correspond to dominant taxa, and the one or more bottom ranked entries in the sorted list L correspond to sparse taxa when the list L is sorted in the decreasing order of the abundance values.

Further, in step 506, minimum number of sparse taxa ($ST_i$) whose cumulative abundance is $\geq i$ % of the total population count 'M' is counted. The abundance values are progressively cumulated in order of an increasing rank of each microbe in the sorted list L when the list L is sorted in the increasing order, or counting minimum number of sparse taxa ($ST_i$) whose cumulative abundance is $\geq i$ % of the total population count 'M' wherein the abundance values are progressively cumulated in a decreasing rank of each microbe in the sorted list L when the list L is sorted in the decreasing order. 'i' is an integer or a fractional number. In one aspect, the predefined range of values of i and j lies in 0 to 50 (such that $0 < i \leq 50$ and $0 < j \leq 50$). In another aspect, the predefined range of values of i and j lies in 0 and 100 (such that $0 < i \leq 100$ and $0 < j \leq 100$).

Further, in step 508, minimum number of dominant taxa ($DT_j$) whose cumulative abundance is $\geq j$ % of the total population count 'M' is counted, wherein the abundance values are progressively cumulated in order of decreasing rank of each microbe in the sorted list L when the list L is sorted in the increasing order, or minimum number of dominant taxa ($DT_j$) whose cumulative abundance is $\geq j$ % of the total population count 'M' are counted wherein the abundance values are progressively cumulated in an increasing rank of each microbe in the sorted list L when the list L is sorted in the decreasing order. 'j' is an integer or a fractional number.

Further, in step 510, repeating the steps 506 and 508 to obtain counts of $ST_i$ and $DT_j$ for a predefined range of values of i and j to generate two sets of values ST and DT respectively, wherein i and j belong to two identical arithmetic progressions within the predefined range. A common difference between consecutive terms of the arithmetic progression is a predefined integer or a predefined fractional value.

Further, in step 512, a Cartesian product of the sets DT and ST is computed to obtain a set C containing a plurality of ordered pairs corresponding to $DT_j$ and $ST_i$ values.

Further, in step 514, a set DSR is derived by computing ($DT_j \div ST_i$) for each ordered pair in the set C. The set DSR is derived by dividing each $DT_j$ term by each $ST_i$ term for a range of values of i and j. Values of i and j varies in the predefined range. The predefined range for i and j is defined such that i+j is equal to 100.

Further, in step 516, the distribution characteristic value of the set 'DSR' is computed. In one example, the distribution characteristic value of the set 'DSR' comprises a central tendency value of the set DSR. The distribution characteristic value of the set DSR further comprises a maximum value of the set DSR, a minimum value of the set DSR, a variance of the set DSR, a skew of the set DSR, or a metric that characterizes modality, symmetry, and variability of distribution of values in the set DSR. In one aspect, the central tendency value for the set 'DSR' is one of a mean, a median, a mode, or any statistical measure that identifies a single value as representative of an entire distribution of values in the set DSR. In one aspect of the disclosure, the distribution characteristic value of the set 'DSR' is computed based on the microbial taxonomic abundance profile, and the risk of the preterm delivery for the pregnant subject is determined based on the distribution characteristic value of the set 'DSR'.

After computing the distribution characteristic value of the set DSR, in step 518, the 'taxonomic composition skew' value is computed by applying a mathematical transformation on the distribution characteristic value. The 'taxonomic composition skew' value is computed by applying the mathematical transformation on the distribution characteristic value comprising the central tendency value of the set DSR. The 'taxonomic composition skew' value is computed by applying the mathematical transformation on the distribution characteristic value of the set DSR, wherein the distribution characteristic value of the set DSR comprises one of a maximum value of the set DSR, a minimum value of the set DSR, a variance of the set DSR, a skew of the set DSR, or a metric that characterizes modality, symmetry, and variability of distribution of values in the set DSR. The mathematical transformation applied on the central tendency value comprises subtraction of the central tendency value from unity, computing an inverse of the central tendency value, or a mathematical transformation method that results in generating a higher numerical value of taxonomic composition skew for a lower central tendency value of the set DSR, and vice versa.

Further, referring to FIG. 4, in step 410, the risk of the preterm delivery for the pregnant subject is determined, by the hardware processor, based on at least one of the central tendency value of the set DSR, the distribution characteristic value of the set DSR, or the taxonomic composition skew value.

Further, in step 412, determining the risk of the preterm delivery for the pregnant subject further comprises categorizing the pregnant subject into one or more risk categories for the preterm delivery, wherein the categorizing is based on at least one of the central tendency value of the set DSR, the distribution characteristic value of the set DSR, or the taxonomic composition skew value. The one or more risk categories comprises a low preterm delivery risk category, a moderate preterm delivery risk category and, a high preterm delivery risk category.

When the microbiome sample is a vaginal microbiome sample obtained from the pregnant woman, the low preterm delivery risk category is indicated for the taxonomic composition skew value greater than 0.922, the moderate preterm delivery risk category is indicated for the taxonomic composition skew value in a range of 0.887 to 0.922, and the high preterm delivery risk category is indicated for the taxonomic composition skew value less than 0.887, and wherein the taxonomic composition skew value is obtained by subtracting from unity, the computed median value of the set DSR.

When the microbiome sample is a vaginal microbiome sample obtained from the pregnant woman, the high preterm delivery risk category is indicated for the central tendency value of the set DSR greater than 0.113, the moderate preterm delivery risk category is indicated for the central tendency value of the set DSR in a range of 0.078 to 0.113, and the low preterm delivery risk category is indicated for the central tendency value of the set DSR less than 0.078, and wherein the central tendency value of the set DSR is a median value of the set DSR.

In one implementation, the steps 502-518, corresponding to computation of the Taxonomic Composition Skew value and the distribution characteristics value of the set DSR, in step 408, are executed by the computation module 212.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

We claim:

1. A method for assessing a risk of preterm delivery for a pregnant subject within first 15 weeks of pregnancy or within a first trimester of the pregnancy to categorize the pregnant subject into one or more risk categories for the preterm delivery, the method comprising:

obtaining a microbiome sample from the pregnant subject, wherein the microbiome sample is obtained from the pregnant subject within the first 15 weeks of pregnancy or within the first trimester of the pregnancy;

obtaining sequenced microbial DNA data from the microbiome sample using a DNA sequencing tool (112);

generating a 'microbial taxonomic abundance profile' for the microbiome sample by computationally analyzing, by the hardware processor (202), the sequenced microbial DNA data using one or more taxonomic classification techniques, and wherein the microbial taxonomic abundance profile contains abundance values of each of a plurality of microbes present in the microbiome sample;

computing, by the hardware processor (202), at least one of a 'Taxonomic Composition Skew' value, and a distribution characteristic value for the 'microbial taxonomic abundance profile', wherein the 'Taxonomic Composition Skew' value, and the distribution characteristic value quantifies biases in the abundance values of the plurality of microbes from the microbial taxonomic abundance profile, wherein the computation of the 'Taxonomic Composition Skew' value and the distribution characteristic value comprises, a) obtaining a total population count 'M' by computing a sum of the abundance values of the plurality of microbes from the microbial taxonomic abundance profile;

b) creating a sorted list 'L' containing the abundance values of each of the plurality of microbes from the microbial taxonomic abundance profile, wherein the sorted list 'L' comprises of the abundance values of each of plurality of microbes present in the microbial taxonomic abundance profile ranked in an increasing order or a decreasing order of the abundance values, and wherein, one or more top ranked entries in the sorted list 'L' correspond to 'sparse taxa', and one or more bottom ranked entries in the sorted list 'L' correspond to 'dominant taxa' when the list L is sorted in the increasing order of the abundance values, and the one or more top ranked entries in the sorted list 'L' correspond to 'dominant taxa', and the one or more bottom ranked entries in the sorted list 'L' correspond to 'sparse taxa' when the list L is sorted in the decreasing order of the abundance values;

c) counting minimum number of 'sparse taxa' ($ST_i$) whose cumulative abundance is ≥i % of the total population count 'M', wherein the abundance values are progressively cumulated in order of an increasing rank of each microbe in the sorted list 'L' when the list L is sorted in the increasing order, or counting minimum number of 'sparse taxa' ($ST_i$) whose cumulative abundance is ≥i % of the total population count 'M', wherein the abundance values are progressively cumulated in order of decreasing rank of each microbe in the sorted list 'L' when the list L is sorted in the decreasing order, and wherein 'i' is an integer or a fractional number;

d) counting minimum number of 'dominant taxa' ($DT_j$) whose cumulative abundance is ≥j % of the total population count 'M', wherein the abundance values are progressively cumulated in order of decreasing rank of each microbe in the sorted list 'L' when the list L is sorted in the increasing order, or counting minimum number of 'dominant taxa' ($DT_j$) whose cumulative abundance is ≥j % of the total population count 'M', wherein the abundance values are progressively cumulated in order of increasing rank of each microbe in the sorted list 'L' when the list L is sorted in the decreasing order, and wherein 'j' is an integer or a fractional number;

e) repeating the steps 'c' and 'd' to obtain counts of $ST_i$ and $DT_j$ for a predefined range of values of 'i' and 'j' to generate two sets of values 'ST' and 'DT' respectively, wherein i and j belong to two identical arithmetic progressions within the predefined range, and wherein a common difference between consecutive terms of the arithmetic progression is a predefined integer or a predefined fractional value;

f) computing a Cartesian product of the sets 'DT' and 'ST' to obtain a set 'C' containing a plurality of ordered pairs corresponding to $DT_j$ and $ST_i$ values;

g) deriving a set 'DSR' by computing ($DT_j \div ST_i$) for each ordered pair in the set 'C';

h) computing the distribution characteristic value of the set 'DSR', wherein the distribution characteristic value of the set 'DSR' comprises a central tendency value of the set DSR;

i) computing the 'taxonomic composition skew' value by applying a mathematical transformation on the distribution characteristic value comprising the central tendency value of the set 'DSR';

determining, by the hardware processor (202), the risk of the preterm delivery for the pregnant subject based on at least one of the central tendency value of the set DSR, the distribution characteristic value of the set 'DSR', or the 'taxonomic composition skew' value to categorize the pregnant subject into one or more risk categories for the preterm delivery based on a predefined threshold of at least one of the central tendency value of the set DSR, the distribution characteristic value of the set 'DSR', or the 'taxonomic composition skew' value, and based on the categorization of the pregnant subject, treating the pregnant subject with at least one of a progesterone supplementation and a cervical cerclage procedure to either reduce or prevent the risk of the preterm delivery.

2. The method of claim 1, wherein the microbiome sample is obtained from the pregnant subject within a second trimester of the pregnancy, wherein the pregnant subject is a pregnant woman.

3. The method of claim 1, wherein the microbiome sample is obtained from the pregnant subject at any time during a period of the pregnancy.

4. The method of claim 1, wherein the pregnant subject is a pregnant woman.

5. The method of claim 1, wherein the pregnant subject is a female viviparous animal.

6. The method of claim 1, wherein the microbiome sample is obtained from a mouth, skin, a gut, a vagina or other body sites of the pregnant subject, and wherein the microbiome sample is selected from a group comprising a vaginal swab sample, a cervical mucus sample, a cervical swab sample, a vaginal swab including swab sample of a fornix, a urine sample, an amniotic fluid sample, a blood sample, a serum sample, a plasma sample, a placental swab, an umbilical swab, a stool sample, a skin swab, an oral swab, a saliva sample, a periodontal swab, a throat swab, a nasal swab, a vesicle fluid sample, a nasopharyngeal swab, a nares swab, a conjunctival swab, a genital swab, a rectum swab, a tracheal aspirate, and a bronchial swab.

7. The method of claim 1 wherein obtaining the sequenced microbial DNA data comprises:

isolating microbial DNA corresponding to the plurality of microbes present in the microbiome sample using at least one DNA extraction technique; and sequencing the microbial DNA using the DNA sequencing tool (112) by applying at least one DNA sequencing technique to obtain the sequenced microbial DNA data.

8. The method of claim 1, wherein generating the 'microbial taxonomic abundance profile' further comprises:

obtaining, via a microbiome sample receiver (110), the microbiome sample from the pregnant subject;

obtaining, via microbiome characterization device (108), microbiome characterization data of the microbiome sample, by applying one or more techniques comprising a microscopic examination, a flow cytometry method, an in-vitro culture based method, one or more enzymatic or fluorescence assays, or one or more assays involving spectroscopic identification and screening of signals from complex microbial populations, wherein the microbiome characterization data comprises a Microscopic imaging data, a Flow cytometry cellular measurement data, a colony count and cellular phenotypic data of microbes grown in in-vitro cultures, a signal intensity data; and generating the 'microbial taxonomic abundance profile' for the microbiome sample by computationally analyzing, by the hardware processor, the microbiome characterization data, using one or more taxonomic classification techniques.

9. The method of claim 7 further comprises at least one of 1) amplifying and sequencing bacterial 16S rRNA or 23S rRNA marker genes from the microbial DNA, 2) amplifying and sequencing either a full-length or one or more specific regions of the bacterial 16S rRNA or 23S rRNA marker genes from the microbial DNA, or 3) amplifying and sequencing one or more phylogenetic marker genes from the microbial DNA.

10. The method of claim 7, wherein the at least one DNA sequencing technique is selected from a next-generation sequencing techniques, wherein the next-generation sequencing techniques comprises a Whole Genome Shotgun (WGS) sequencing, a fragment library based sequencing technique, a mate-pair library or a paired-end library based sequencing technique, or a combination thereof.

11. The method of claim 1, wherein the predefined range of values of 'i' and 'j' lies in a range of 0 to 100, and wherein the predefined range of i and j is defined such that i+j is equal to 100.

12. The method of claim 1, wherein the taxonomic composition skew takes a value in a range of 0 to 1.

13. The method of claim 1, wherein the central tendency value for the set 'DSR' is one of a mean, median, mode, or any statistical measure that identifies a single value as representative of an entire distribution of values in the set DSR.

14. The method of claim 1, wherein the distribution characteristic value of the set DSR comprises one of a maximum value of the set DSR, a minimum value of the set DSR, a variance of the set DSR, a skew of the set DSR, or a metric that characterizes modality, symmetry, and variability of distribution of values in the set DSR.

15. The method of claim 1, wherein the mathematical transformation applied on the central tendency value comprises one of subtraction of the central tendency value from unity, computing an inverse of the central tendency value, or a mathematical transformation method that results in generating a higher numerical value of taxonomic composition skew for a lower central tendency value of the set DSR, and vice versa.

16. The method of claim 1, wherein the one or more risk categories comprises a low preterm delivery risk category, a moderate preterm delivery risk category and, a high preterm delivery risk category.

17. The method of claim 16, wherein for a vaginal microbiome sample obtained from a pregnant woman, the low preterm delivery risk category is indicated for the 'taxonomic composition skew' value greater than 0.922, the moderate preterm delivery risk category is indicated for the 'taxonomic composition skew' value in a range of 0.887 to 0.922, and the high preterm delivery risk category is indicated for the 'taxonomic composition skew' value less than 0.887, and wherein the 'taxonomic composition skew' value is obtained by subtracting from unity, the computed median value of the set DSR.

18. The method of claim 16, wherein for a vaginal microbiome sample is obtained from a pregnant woman, the high preterm delivery risk category is indicated for the central tendency value of the set DSR greater than 0.113, the moderate preterm delivery risk category is indicated for the central tendency value of the set DSR in a range of 0.078 to 0.113, and the low preterm delivery risk category is indicated for the central tendency value of the set DSR less than 0.078, and wherein the central tendency value of the set DSR is a median value of the set DSR.

19. The method of claim 1, wherein the pre-defined threshold value is computed by analyzing the microbiome data obtained from a cohort of pregnant subjects.

* * * * *